(12) United States Patent
Gozes et al.

(10) Patent No.: US 9,518,994 B2
(45) Date of Patent: Dec. 13, 2016

(54) METHOD FOR DIAGNOSING AND MONITORING SCHIZOPHRENIA AND TAUOPATHIES

(75) Inventors: Illana Gozes, Ramat-Hasharon (IL); Efrat Dresner, Holon (IL)

(73) Assignee: Ramot at Tel Aviv University, Tel Aviv (IL)

( * ) Notice: Subject to any disclaimer, the term of this patent is extended or adjusted under 35 U.S.C. 154(b) by 284 days.

(21) Appl. No.: 13/520,390

(22) PCT Filed: Jan. 4, 2011

(86) PCT No.: PCT/IL2011/000004
§ 371 (c)(1),
(2), (4) Date: Mar. 5, 2013

(87) PCT Pub. No.: WO2011/083461
PCT Pub. Date: Jul. 14, 2011

(65) Prior Publication Data
US 2013/0164743 A1    Jun. 27, 2013

Related U.S. Application Data

(60) Provisional application No. 61/292,799, filed on Jan. 6, 2010.

(51) Int. Cl.
*C12Q 1/68* (2006.01)
*C12P 19/34* (2006.01)
*G01N 33/68* (2006.01)

(52) U.S. Cl.
CPC ... *G01N 33/6896* (2013.01); *G01N 2800/2814* (2013.01); *G01N 2800/2835* (2013.01); *G01N 2800/302* (2013.01)

(58) Field of Classification Search
None
See application file for complete search history.

(56) References Cited

U.S. PATENT DOCUMENTS

| 6,613,740 | B1 | 9/2003 | Gozes et al. |
| 6,649,411 | B2 | 11/2003 | Gozes et al. |
| 6,933,277 | B2 | 8/2005 | Brenneman et al. |
| 7,264,947 | B2 | 9/2007 | Gozes et al. |
| 7,384,908 | B1 | 6/2008 | Brenneman et al. |
| 7,427,590 | B2 | 9/2008 | Brenneman et al. |
| 7,427,598 | B2 | 9/2008 | Spong et al. |
| 7,452,867 | B2 | 11/2008 | Gozes et al. |
| 7,863,247 | B1 | 1/2011 | Brenneman et al. |
| 2007/0054847 | A1 | 3/2007 | Gozes et al. |
| 2008/0194488 | A1 | 8/2008 | Gozes et al. |
| 2009/0124543 | A1 | 5/2009 | Gozes et al. |
| 2009/0137469 | A1 | 5/2009 | Gozes et al. |
| 2009/0170780 | A1 | 7/2009 | Gozes et al. |
| 2009/0203615 | A1 | 8/2009 | Spong et al. |
| 2009/0247457 | A1 | 10/2009 | Brenneman et al. |
| 2010/0216723 | A1 | 8/2010 | Gozes et al. |

FOREIGN PATENT DOCUMENTS

WO    WO 98/35042 A1    8/1998

OTHER PUBLICATIONS

Chan (Drug Discovery and Development, Apr. 2006; vol. 6, from the web: pp. 1-6.*
Dracheva et al; Am J. Psychiatry 2001, vol. 158, pp. 1400-1410.*
Dracheva et al; Journal of Neuroscience Research, vol. 76, pp. 581-592, 2004.*
Slonin, Nature Genetics Supplement, vol. 32, Dec. 2002, pp. 502-508.*
Michiels et al. Lancet, 2005; 365:488-492.*
Cheung et al (Nature Genetics, vol. 33, pp. 422-425; (2003).*
Enard et al (Science. Apr. 12, 2002; 296(5566):340-43).*
Hoshikawa et al (Physiol Genomics, vol. 12, 209-219; (2003)).*
International Search Report from PCT/IL2011/000004, dated Jan. 24, 2012(6 pages).
Fernandez-Montesinos et al.; "Activity-dependent neuroprotective protein (ADNP) expression in the amyloid precursor protein/presenilin 1 mouse model of Alzheimer's disease"; *J. Mol. Neurosci*; 41(1):114-120 (May 2012) ePub Oct. 21, 2009.

\* cited by examiner

*Primary Examiner* — Jehanne Sitton
(74) *Attorney, Agent, or Firm* — Kilpatrick Townsend & Stockton LLP

(57) ABSTRACT

The present invention provides methods and kits for diagnosing or monitoring conditions such as schizophrenia and tauopathies in a patient by determining the level of ADNP1 or ADNP2 in a sample from the patient.

18 Claims, 10 Drawing Sheets

METHOD FOR DIAGNOSING AND MONITORING SCHIZOPHRENIA AND TAUOPATHIES

RELATED APPLICATIONS

This application is the U.S. National Stage entry of International Application No. PCT/IL2011/000004, filed Jan. 4, 2011, which claims priority to U.S. Provisional Patent Application No. 61/292,799, filed Jan. 6, 2010, the contents of each are incorporated by reference in their entirety.

BACKGROUND OF THE INVENTION

Neurodegenerative conditions affect a significant portion of our society, especially among the aging population. Various tauopathies, including Alzheimer's disease, can lead to neurodegeneration. It is estimated that Alzheimer's disease currently affects 2.4 million to 4.5 million Americans, and this number is projected to more than triple to reach 16 million by mid-century. Although Alzheimer's disease is not a normal part of aging, the risk of developing the illness rises with age. Current research from the National Institute on Aging indicates that the prevalence of Alzheimer's disease doubles every five years beyond age 65. This disease impacts an increasingly larger percentage of Americans, as the number of people age 65 and older will reach 70.3 million by 2030, or 20% of the U.S. population; likewise, those 85 and older will rise to 8.9 million, according to the U.S. Census Bureau. To consider the impact of this disease from another perspective, it often requires one to four family members to act as caregivers for each individual with Alzheimer's disease.

Mental disorders affects our society in a similar manner. For example, schizophrenia, a disabling mental disease affecting approximately 1% of the world population and over 2 million people in America, is devastating for those who are afflicted and their families. Treating and maintaining patients suffering from schizophrenia is very costly for the families and society. In 2002, the cost for treating schizophrenia in the US alone was estimated to be $62.7 billion.

Because of the significant social and economical impact of neurodegenerative diseases and mental disorders, there exists a need for new and better methods for the diagnosis and monitoring of these conditions. The present invention fulfills these and other related needs.

BRIEF SUMMARY OF THE INVENTION

In one aspect, the present invention provides a method for diagnosing or monitoring a tauopathy in a patient. The method comprises the step of determining ADNP level in a sample from the patient. In some embodiments, the sample is a brain sample (such as a sample taken from the hippocampus or frontal cortex of the brain) or a blood sample (which may be a whole blood (lymphocytes), plasma, or serum sample) or cerebrospinal fluid (CSF). In some embodiments, the ADNP level is the amount of ADNP protein. In other embodiments, the ADNP level is the amount of ADNP mRNA. In the alternative, the ADNP level may be the ratio of ADNP protein to ADNP2 protein in the same sample, or the ADNP level may be the ratio of ADNP mRNA to ADNP2 mRNA in the same sample. The tauopathy to be detected may be Alzheimer's disease, Parkinson's disease, frontotemporal dementia, corticobasal degeneration, frontotemporal lobar degeneration, progressive supranuclear palsy, amyotrophic lateral sclerosis, Creutzfeldt-Jakob disease, Down's syndrome, Frontotemporal dementia with Parkinsonism linked to chromosome 17, or Multiple system atrophy.

In some embodiments, the method includes a step where the ADNP level is compared with a standard control, and an increase in the ADNP level from the control indicates the presence of a tauopathy. In some cases, the step of determining the ADNP level is performed at least twice, especially when at least once earlier an increase in the ADNP level as compared to the control level was observed. In these repeated steps of measuring ADNP level, a trend of decline in the ADNP level indicates improvement of the tauopathy and a trend of incline in the ADNP2 level indicates worsening of the tauopathy.

In another aspect, the present invention provides a kit for diagnosing or monitoring a tauopathy in a patient. The tauopathy to be detected or monitored may be Alzheimer's disease, Parkinson's disease, frontotemporal dementia, corticobasal degeneration, frontotemporal lobar degeneration, progressive supranuclear palsy, amyotrophic lateral sclerosis, Creutzfeldt-Jakob disease, Down's syndrome, Frontotemporal dementia with Parkinsonism linked to chromosome 17, or Multiple system atrophy. The kit contains (1) a first agent that specifically binds ADNP mRNA or protein and (2) a standard control representing average ADNP or ADNP2 level in a sample from a healthy individual. The sample may be a brain sample, a whole blood sample (lymphocytes), a plasma sample, a serum sample or a CSF sample. In some cases, the kit may further include a second agent that specifically binds ADNP2 mRNA or protein. In some cases, the standard control represents the average ratio of ADNP mRNA to ADNP2 mRNA in a sample from a healthy individual; whereas in other cases, the standard control represents the average ratio of ADNP protein to ADNP2 protein in a sample from a healthy individual. Optionally, the kit contains multiple standard controls representing average ADNP levels in different samples taken from the healthy individual, such as samples taken from different parts of a healthy individual's brain, e.g., hippocampus or frontal cortex. Typically, the kit also includes user instruction material for the proper use of the kit. Furthermore, the kit provides an assay for neuroprotective activity, offering a useful tool in monitoring clinical trials associated with neuroprotection studies.

In yet another aspect, the present invention provides a method diagnosing or monitoring schizophrenia in a patient. The method comprises the step of determining ADNP and ADNP2 level in a sample from the patient. In some embodiments, the sample is a brain sample, cerebrospinal fluid sample or a blood sample. The brain sample may be taken from various parts of the brain, such as the hippocampus or frontal cortex of the patient and cerebrospinal fluid (CSF). The blood sample may be a whole blood (lymphocytes), plasma, or serum sample. In some embodiments, the ADNP and ADNP2 level is the amount of ADNP2 or ADNP protein or ADNP2 or ADNP mRNA in the sample; whereas in other embodiments, the ADNP2 level is the ratio of ADNP2 protein to ADNP protein in the same sample, or the ADNP2 level is the ratio of ADNP2 mRNA to ADNP mRNA in the same sample.

In some embodiments, the method includes a step where the ADNP or ADNP2 level is compared with a standard control, and an increase in the ADNP or ADNP2 level (e.g., the protein level of ADNP or ADNP2, or the mRNA level of ADNP or ADNP2) from the control indicates the presence of schizophrenia. In some cases, the step of determining the ADNP or ADNP2 level (e.g., the protein level of ADNP or ADNP2, or the mRNA level of ADNP or ADNP2) is performed at least twice, especially when at least once earlier an increase in the ADNP or ADNP2 level as compared to the control level was observed. In these repeated steps of measuring ADNP or ADNP2 level (e.g., the protein level of ADNP or ADNP2, or the mRNA level of ADNP or ADNP2), a trend of decline in the ADNP or ADNP2 level indicates improvement of schizophrenia and a trend of incline in the ADNP or ADNP2 level indicates worsening of schizophrenia.

In a further aspect, the present invention provides a kit for diagnosing or monitoring schizophrenia in a patient. The kit contains (1) a first agent that specifically binds ADNP and ADNP2 mRNA or ADNP and ADNP2 protein and (2) a standard control representing average ADNP and ADNP2 level in a sample from a healthy individual. The sample may be a brain sample (such as one taken from the hippocampus or frontal cortex of the brain), a whole blood sample, a plasma sample, a serum sample, or a CSF sample. The kit may further comprise a second agent that specifically binds ADNP mRNA or protein. In some cases, the standard control represents the average ratio of ADNP2 mRNA to ADNP mRNA in a sample from a healthy individual; whereas in other cases, the standard control represents the average ratio of ADNP2 protein to ADNP protein in a sample from a healthy individual. Optionally, the kit may comprise multiple standard controls representing average ADNP or ADNP2 levels in different samples taken from a healthy individual. For example, the different samples may be taken from different parts of a healthy individual's brain, such as the hippocampus and frontal cortex. Typically, the kit will further contain an instruction material to direct users for properly using the kit.

DEFINITIONS

Figure 1A:
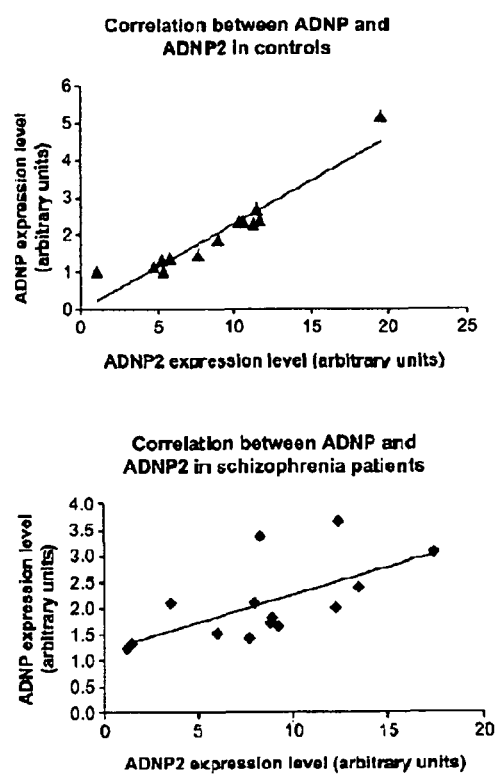
FIG. 1: A. Graphic representation of ADNP and ADNP2 correlation in controls (A) and schizophrenia patients (B). Quantitative real time polymerase chain reaction (qPCR) results shows that in the normal, control situation ADNP expression was correlated with ADNP2 expression. In a control population aged 46.6±15.4 (Mean±S.D.) years, hippocampal ADNP to ADNP2 transcript correlation was r=0.931 (p<0.001, n=14). In the hippocampus of schizophrenia patients this correlation was dramatically decreased to r=0.637 (p=0.014, n=14). B. Graphic representation of the correlation between hippocampal ADNP and ADNP2 mRNA levels vs. Disease duration of illness—DOI (A) and age (B) in schizophrenia patients. A correlation between DOI and ADNP2 mRNA levels was observed in the hippocampus of the schizophrenia patients group (r=0.637, p=014, n=14, Pearson's correlation.

The term "activity-dependent neuroprotective protein (ADNP)" refers to an activity dependent neurotrophic factors (ADNF) that has neurotrophic/neuroprotective activity as measured with in vitro cortical neuron culture assays described by, e.g., Hill et al., *Brain Res.* 603, 222-233 (1993); Gozes et al., *Proc. Natl. Acad. Sci. USA* 93, 427-432 (1996). Full length human ADNP has a predicted molecular weight of 123,562.8 Da (>1000 amino acid residues) and a theoretical pI of about 6.97. ADNP gene is localized to human chromosome 20q13.13-13.2, a region associated with cognitive function. Full-length amino acid and nucleic acid sequences of ADNP can be found in WO 98/35042, WO 00/27875, U.S. Pat. Nos. 6,613,740 and 6,649,411. The Accession number for the human sequence is NP 852107. The term "ADNP2" refers to a homolog of ADNP assigned to human chromosome 18q23, a region associated with psychiatric disorder. See, e.g., Zamostiano et al., *J. Biol. Chem.* 276(1):708 (2001); Kushnir et al., *J Neurochem,* 105: 537-545 (2008); Van Broeckhoven, C. and Verheyen, G. *Am J Med Genet,* 88: 263-270 (1999). In this application, the term "ADNP1" is used interchangeably with "ADNP," in some cases to more clearly distinguish from ADNP2.

The terms "level of ADNP" and "ADNP level" are used interchangeably to encompass the amount of ADNP protein, the amount of ADNP mRNA, the ratio between the ADNP protein and ADNP2 protein, and the ratio between the ADNP mRNA and ADNP2 mRNA found in a biological sample taken from an individual. Similarly, the terms "level of ADNP2" and "ADNP2 level" are used interchangeably to encompass the amount of ADNP2 protein, the amount of ADNP2 mRNA, the ratio between the ADNP2 protein and ADNP protein, and the ratio between the ADNP2 mRNA and ADNP mRNA found in a biological sample taken from an individual.

The term "subject" refers to any mammal, in particular human, at any stage of life. The term "contacting" is used herein interchangeably with the following: combined with, added to, mixed with, passed over, incubated with, flowed over, etc.

The term "tauopathy" refers to a disease belonging to a class of neurodegenerative disorders caused by pathological aggregation of the tau protein in the so-called neurofibrillary tangles (NFT) in the human brain. Included in the general definition of tauopathies are Alzheimer's disease, Parkinson's disease, frontotemporal dementia, corticobasal degeneration, frontotemporal lobar degeneration (Pick's disease), progressive supranuclear palsy (PSP), amyotrophic lateral sclerosis (ALS, often referred to as Lou Gehrig's Disease), Creutzfeldt-Jakob disease, Down's syndrome, Frontotemporal dementia with parkinsonism linked to chromosome 17, and Multiple system atrophy.

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder and attention deficit disorders) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV). Typically, such disorders have a complex genetic and/or a biochemical component.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to VH—CH1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The term "average," as used in the context of describing an individual not suffering from any neurodegenerative disease or mental disease, refers to certain characteristics, such as the level of ADNP protein or mRNA, or the level of ADNP2 protein or mRNA, found in the subject's biological samples (e.g., whole blood, serum, plasma, and tissue samples taken from various parts of the brain) that are representative of a randomly selected group of healthy persons not suffering from or at risk of developing any neurodegenerative or mental disorder. This selected group typically comprises a sufficient number of healthy individuals such that the average level of ADNP or ADNP2 among these individuals reflects, with reasonable accuracy, the level of ADNP or ADNP2 in the general population of healthy persons who are not suffering from or at risk of developing neurodegenerative or mental disorders. In addition, the selected group of individuals may, optionally, have similar aspects in medical history, as well as in age, gender, and genetic background, etc.; while in other cases no such similarity is required for establishing an average level of ADNP or ADNP2, either in protein, mRNA, or the ratio between the two.

A "standard control" as used herein refers to a sample suitable for the use as a comparison basis in a method of the present invention, in order for determining whether an increase or decrease exists in the level of ADNP or ADNP2 protein or mRNA found in a sample from a healthy subject, e.g., in the serum sample, CSF sample or brain tissue sample. Such sample contains a known level of the ADNP or ADNP2 protein or mRNA that closely reflects the average level of ADNP or ADNP2 protein or mRNA in an average individual who is not suffering from a neurodegenerative or mental disorder or at risk of developing such a disorder, as described above. In some cases, a "standard control" is reflective of the average ADNP or ADNP2 level in a particular type of sample, e.g., a tissue sample from a particular of the brain.

"An increase or a decrease from the standard control" as used herein refers to a positive or negative change in quantity from the standard control. An increase is typically at least 10%, or at least 20%, or 50%, or 100%, and can be as high as at least 2-fold or at least 5-fold or even 10-fold. Similarly, a decrease is typically at least 10%, or at least 20%, 30%, or even as high as 50% or more in reduction from the level of the standard control.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"PCR primers" as used herein refer to oligonucleotides, typically in pairs, that can be used in a polymerase chain reaction (PCR) to amplify a nucleotide sequence originated from an mRNA encoding a protein of interest, such as human ADNP or ADNP2. Typically, at least one of the PCR primers for amplification of a nucleotide sequence encoding ADNP or ADNP2 protein should be sequence-specific for the protein.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by readthrough transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "biological sample" or "sample" includes any section of tissues such as biopsy and autopsy samples, and frozen sections taken for histological purposes. Such samples include blood and blood fractions or products (e.g., serum, plasma, platelets, red blood cells, and the like), other bodily fluids (such as cerebral spinal fluid or CSF, urine, saliva, oral washings, reproductive tract washings, and sweat), sputum, tissue (such as brain tissue, e.g., hippocampus, cortex, and cerebellum), cultured cells, e.g., primary cultures, explants, and transformed cells, stool, urine, etc. A biological sample of this invention is obtained from a mammal such as a primate (e.g., chimpanzee or human); cow; dog; cat; rodent (e.g., guinea pig, rat, or mouse); rabbit; and the like.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (i.e., blood cells or brain tissue), the size of the desired sample, among other factors. Representative biopsy techniques include excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tissue. A diagnosis or prognosis made by endoscopy or fluoroscopy can require a "core-needle biopsy" of the tissue, or a "fine-needle aspiration biopsy," which generally obtains a suspension of cells from within the tissue. Biopsy techniques are discussed, for example, in *Harrison's Principles of Internal Medicine*, Kasper, et al., eds., 16th ed., 2005, Chapter 70, and throughout Part V.

The phrase "specifically binds," when referring to a protein or peptide, refers to a binding reaction that is determinative of the presence of the protein in a heterogeneous population of proteins and other biologics. Thus, under designated immunoassay conditions, the specified binding agent (e.g., an antibody) binds to a particular protein at least two times the background and does not substantially bind in a significant amount to other proteins present in the sample. Specific binding to an antibody under such conditions may require an antibody that is selected for its specificity for a particular protein or a protein but not its similar "sister" proteins. For example, antibodies may be raised to specifically bind ADNP protein but not ADNP2 protein. In the alternative, antibodies can be raised and selected to specifically bind ADNP2 protein but not ADNP protein. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background.

DETAILED DESCRIPTION OF THE INVENTION

I. Introduction

The present inventors discovered a correlation between the expression levels of ADNP and ADNP2 and the presence or severity of neurodegenerative diseases such as tauopathies (e.g., Alzheimer's disease and progressive supranuclear palsy-PSP) and mental disorders such as schizophrenia. This invention therefore provides, for the first time, methods and kits for detecting these conditions in a patient and for assessing disease progression in the patient by monitoring the level of ADNP or ADNP2, often compared with a standard control established from an average healthy individual not suffering from these conditions, and optionally monitoring the levels over time within the same patient to determine the progression of the disease or effectiveness of the treatment given to the patient. In some cases, the ratio between ADNP and ADNP2, either at the protein level or mRNA level, will provide particularly valuable information for diagnostic and prognostic purposes.

II. Preparing Test Samples

A. Obtaining Samples

The first step of practicing the present invention is to obtain a sample from a subject being tested, e.g., a brain tissue sample, CSF sample or a blood sample, especially a serum, lymphocytes or plasma sample, from a patient for detecting or monitoring a pertinent condition (e.g., Alzheimer's disease, PSP or schizophrenia) using a method of the present invention. The specific methods for taking test samples vary depending on the site or sites where the samples are taken. Standard procedures routinely employed in hospitals or clinics are typically followed for this purpose. For example, collection of blood samples from a patient is performed on a daily basis in a medical office. An appropriate amount of sample, e.g., between 5 to 20 ml of peripheral blood, is collected and maybe stored according to standard medical laboratory testing procedure prior to further preparation.

Human lymphocytes are isolated from 10 ml of venous blood using the Ficoll Paque method. CSF is obtained by standard preparation procedures.

B. Preparing Samples for ADNP/ADNP2 Detection

The serum or plasma of a blood sample from a subject is suitable for the present invention and can be obtained by well known methods. For example, a blood sample can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum is obtained through centrifugation following blood clotting. Centrifugation is typically conducted at an appropriate speed, e.g., 1,500-3,000×g, in a chilled environment, e.g., at a temperature of about 4-10° C. Plasma or serum may be subject to additional centrifugation steps before being transferred to a fresh tube for measuring the ADNP or ADNP2 level, either in protein or mRNA amount. Preparation of other tissue samples from a patient, such as brain tissue samples, is carried out according to known methods for measuring protein or mRNA concentration in a tissue sample or according to methods described in this application.

In certain applications of this invention, plasma or serum may be the preferred sample types. In other applications of the present invention, whole blood may be preferable. In yet other applications, brain tissue samples from a test subject, such as samples taken from hippocampus or frontal cortex, may be preferable. Human lymphocytes are isolated from 10 ml of venous blood using the Ficoll Paque method. CSF is obtained by standard preparation procedures.

III. Determining ADNP/ADNP2 Level

A biological sample from a subject is assessed for the level of ADNP/ADNP2, including the protein or mRNA amount or concentration in the sample, in the practice of the present invention. Suitable biological samples include, but are not limited to, blood (especially serum or plasma) and brain tissues taken from different parts of the brain. Preference for a sample from a particularly tissue type depends largely on the purpose of the testing.

A. Determining ADNP/ADNP2 Protein Level

ADNP or ADNP2 protein can be detected using a variety of immunological assays. In some embodiments, a sandwich assay can be performed by capturing ADNP or ADNP2 protein from a test sample with an antibody having specific binding affinity for ADNP or ADNP2 protein. ADNP or ADNP2 protein then can be detected with a labeled antibody having specific binding affinity for ADNP or ADNP2 protein, respectively. ADNP and ADNP2 can also be detected by western blot analysis using specific antibodies. Labeling cellular ADNP and ADNP2 by fluorescent antibodies in the presence of saponin permeabilization followed by flow cytometry can also be used for blood cells. Alternatively, standard immunohistochemical techniques can be used to detect ADNP or ADNP2 protein, using such antibodies. Both monoclonal and polyclonal antibodies (including antibody fragment with desired binding specificity) can be used for specific detection of ADNP or ADNP2 protein. Such antibodies and their binding fragments with specific binding affinity to ADNP or ADNP2 protein can be generated by known techniques.

B. Determining ADNP/ADNP2 mRNA Level

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of ADNP or ADNP2 mRNA may be quantified. The preferred method for determining the mRNA level is an amplification-based method, e.g., by polymerase chain reaction (PCR).

Prior to the amplification step, a DNA copy (cDNA) of the ADNP or ADNP2 mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available. Quantitative real time PCR (qPCR) follows the general principle of PCR; its key feature is that the amplified DNA is detected as the reaction progresses in real time. This approach differs from standard PCR, where the product of the reaction is detected at its end. Two common methods for detection of products in real-time PCR are: (1) non-specific fluorescent dyes that intercalate with any double-stranded DNA, and (2) sequence-specific DNA probes that are labeled with fluorescent reporter which permits detection only after hybridization of the probe with its complementary DNA target.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

2. Other Quantitative Methods

The ADNP or ADNP2 mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques, the presence of a band of the same size as the standard control is an indication of the presence of a target mRNA, the amount of which may then be compared to the control based on the intensity of the band. Alternatively, oligonucleotide probes specific to ADNP or ADNP2 mRNA can be used to detect the presence of such mRNA species and indicate the amount of mRNA in comparison to the standard control, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

IV. Establishing a Standard Control

In order to establish a standard control, a group of healthy subjects without any known neurodegenerative or mental disorders is first to be selected. These individuals may optionally have the same gender, same or similar age, biological features (e.g., ethnic background), and/or medical history. The neurological and/or mental health status of the selected individuals should be confirmed by well established, routinely employed methods.

Furthermore, the selected group of individuals free of neurodegenerative or mental disorders should be of a reasonable size, such that the average level of ADNP or ADNP2 calculated from the group can be reasonably regarded as representative of the normal or average level of ADNP or ADNP2 among the general population of healthy individuals of the species. Preferably, the selected group comprises at least 10 subjects. Typically, an average level of ADNP or ADNP2 is established for each distinct type of tissue sample.

Once an average value is established for the level of ADNP or ADNP2 based on the individual values found in each individual of the selected group, this values is considered a standard for the ADNP or ADNP2 level for this type of sample, which may be limited to the specific tissue and/or anatomic site. Any biological sample such as a serum or CSF sample that contains an ADNP or ADNP2 level similar to the average can thus be used as a standard control. A solution containing ADNP or ADNP2 at a level similar to the established average of ADNP or ADNP2 level can also be artificially assembled and serve as a standard control.

V. Assessing Neurodegeneration or Mental Disorder

Once the level of ADNP or ADNP2 is determined from a test sample, the state of neurodegeneration or mental disorder in the subject being tested can then be assessed. In general, a lower level of ADNP2 level, particularly a changed ratio of ADNP2 mRNA over ADNP mRNA, as compared with a control value, indicates the presence or an increased risk of schizophrenia in the subject. Monitoring the state or severity of schizophrenia by monitoring changes in the amount of ADNP2 and ADNP protein or mRNA, or the ratio of ADNP2 over ADNP (both in protein and mRNA) in a suitable biological sample (e.g., serum, CSF or a brain tissue sample) over a time period, especially after the patient has already had a previous test result indicating a likely diseased state, can provide information relating the progression of the disease and the effectiveness of therapy the patient is receiving.

Similarly, monitoring and comparing ADNP level to a standard control can also indicate the presence or status of a neurodegerative disorder, such as tauopathies including Alzheimer's Disease. In general, a higher level of ADNP, as compared with the control value, indicates the presence or worsening of the tauopathy. An incline or decline from the previously measured ADNP level (especially one that carries the implication of a diseased state) will indicate the progression of the neurodegenerative disorder and/or the effectiveness of the treatment given to the patient.

VI. Kits

The invention provides compositions and kits for practicing the methods described herein to assess the presence or state of a neurodegenerative disorder or mental disorder in a subject, which can be used for various purposes such as providing information for designing and adjusting therapeutic plans.

Kits for carrying out the immunoassays for determining ADNP or ADNP2 protein amount or concentration typically include a detection agent that comprises an antibody (a polyclonal or monoclonal antibody, or an antiserum) that specifically binds to the target protein. Optionally, a detectable label is conjugated to the detection agent for indicating the presence of the agent and therefore the ADNP or ADNP2 protein. In some cases, the kits may include multiple antibodies for detection purposes. For examples, a primary antibody and a secondary antibody may be included in the kits, with the primary antibody having a binding specificity for the ADNP or ADNP2 protein, and the secondary antibody having a binding specificity for the primary antibody and having a detectable label or moiety.

Kits for carrying out assays for determining ADNP or ADNP2 mRNA amount or concentration typically include at least one oligonucleotide useful for specific hybridization with the ADNP or ADNP2 coding sequence or complementary sequence. Optionally, this oligonucleotide is labeled with a detectable moiety. In some cases, the kits may include at least two oligonucleotide primers that can be used in the amplification of ADNP or ADNP2 mRNA by PCR, particularly by RT-qPCR.

Typically, the kits also provide instruction manuals to guide users in analyzing test samples and assessing the presence or severity of a neurodegenerative disorder (e.g., Alzheimer's disease, progressive supranuclear palsy or other tauopathies) or a mental disorder (e.g., schizophrenia) in a test subject.

EXAMPLES

The following examples are provided by way of illustration only and not by way of limitation. Those of skill in the art will readily recognize a variety of non-critical parameters that could be changed or modified to yield essentially the same or similar results.

Example 1

Activity-Dependent Neuroprotective Protein (ADNP) Expression Level is Correlated with the Expression of the Sister Protein ADNP2: Deregulation in Schizophrenia Activity-dependent neuroprotective protein (ADNP) is an essential protein for brain formation and partial knockdown of ADNP results in reduced neurite outgrowth, reduced neuroprotection, in vivo tauopathy and neuronal cell death. ADNP contains a small motif, NAPVSIPQ (termed NAP) that provides potent neurotrophic and neuroprotective activities, partially ameliorating ADNP-related deficiencies. ADNP2 is an ADNP homologue that is required for cell viability, but does not contain the NAP motif. In this study, it was investigated whether a major disease associated with synaptic dysfunction and microtubule impairment like schizophrenia exhibits ADNP/ADNP2 transcript deregulation. Quantitative real time polymerase chain reaction (qPCR) results showed that in the normal, control situation ADNP expression was correlated with ADNP2 expression. Thus, in a control population aged 46.6±15.4 (Mean±S.D.) years, hippocampal ADNP to ADNP2 transcript correlation was r=0.931 (p<0.001, n=14). The same high level of correlation was maintained in the differentiating neuronal-glial mouse cell model—P19, the original source of ADNP (r=0.98, p=001). In the hippocampus of schizophrenia patients this correlation was dramatically decreased to r=0.637 (p=0.014, n=14) and the decrease was significantly associated with disease duration with an almost 2-fold increase in ADNP2 expression. It is worthwhile to mention that in the frontal cortex of the same schizophrenia patients there was a much higher correlation between ADNP and ADNP2 (r=0.854, p<0.001, n=12) than in the hippocampus, a phenomenon which may reflect difference in ADNP and ADNP2 equilibrium between these two brain regions in schizophrenia. Together, these results indicate an imbalance in ADNP/ADNP2 expression as a factor impacting disease progression in schizophrenia.

Introduction

Activity-dependent neuroprotective protein (ADNP) is an essential protein for brain formation. Complete ADNP knock out in mice results in the inhibition of neural tube closure and death at embryonic age 8.5-9.5, A. Pinhasov et al., *Brain Res Dev Brain Res* 144, 83-90 (2003; S. Mandel et al., *Dev Biol* 303, 814-824 (2007). Previous studies using Affymetrix 22,690-oligonucleotide-based microarrays on ADNP knockout and control mouse embryos (E9) separated completely from extra embryonic tissue showed marked differences in expression profiles between ADNP-deficient embryos and ADNP-expressing embryos. A group of dramatically up-regulated gene transcripts in the ADNP-deficient embryos were clustered into a family encoding for proteins enriched in the visceral endoderm such as apolipoproteins, cathepsins and methallotionins and a down regulated gene cluster associated with ADNP-deficiency consisted of organogenesis markers including neurogenesis (Ngfr, neurogenin1, neurod1) and heart development (Myl2). These results placed ADNP at a crucial point of gene regulation, repressing potential endoderm genes and enhancing genes associated with organogenesis/neurogenesis, S. Mandel et al. *Dev Biol* 303, 814-824 (2007). In order to further investigate the involvement of ADNP in the neuro-differentiation process, small hairpin RNA directed against it was transfected into P19 cells, pluripotent teratocarcinoma cell line that can differentiate into neuroglial phenotype under treatment with retinoic acid. A ~80% reduction in ADNP led to a substantial reduction in embryoid body formation and a significant reduction (~50%) in neurite numbers. These results position ADNP in direct association with neuronal cell differentiation and maturation, and further suggest the possibility of association of ADNP with neuronal plasticity and attainment of active morphology in the adult, S. Mandel et al. *J Mol Neurosci* 35, 127-141 (2008). In addition, ADNP directly interacts with the chromatin remodeling complex SWI/SNF (mating type switching/sucrose nonfermenting) that is associated with the acquisition of proper cell morphology, S. Mandel and I. Gozes. *J Biol Chem* 282, 34448-34456 (2007): Under conditions of oxidative stress, recombinant ADNP provides neuroprotection, R. A. Steingart and I. Gozes. *Mol Cell Endocrinol* 252, 148-153 (2006). In vivo, the expression of ADNP shows estrous-cycle related fluctuations in the arcuate nucleus of the hypothalamus, a brain area that shows plasticity during the estrous cycle, S. Furman et al. *Neurosci Lett* 373, 73-78 (2005). Partial knockdown of ADNP in mice results in tauopathy, neuronal cell death and cognitive dysfunction, I. Vulih-Shultzman et al. *J Pharmacol Exp Ther* 323, 438-449 (2007).

ADNP contains a small motif, NAPVSIPQ (termed NAP) (M. Bassan et al. *J Neurochem* 72, 1283-1293 (1999)), that provides potent neurotrophic (I. Gozes and I. Spivak-Pohis. *Curr. Alzheimer Res* 3, 197-199 (2006) and neuroprotective activities, partially ameliorating ADNP-related deficiencies (I. Vulih-Shultzman et al. *J Pharmacol Exp Ther* 323, 438-449 (2007)). The underlying mechanism for NAP neuroprotection is by interacting with the microtubule cytoskeleton, thus protecting microtubules function. Affinity chromatography identified tubulin, the subunit protein of microtubules, as a NAP-interacting protein. Further studies have shown that treatment of neuronal and glial cells with NAP, results in a rapid microtubule re-arrangement that provides protection against microtubule-zinc intoxication (I. Divinski et al. *J Biol Chem* 279, 28531-28538 (2004; I. Divinski et al. *J Neurochem* 98, 973-984 (2006)) and rapidly reverses nocodazole-induced microtubule depolymerization (I. Gozes and I. Divinski. *Curr Alzheimer Res* 4, 507-509 (2007)). ADNP itself was found to co-localize with tubulin in astrocytes (S. Furman et al. *Neuron Glia Biology* 1, 193-199 (2004)). ADNP2 is an ADNP homologue (R. Zamostiano et al. *J Biol Chem* 276, 708-714 (2001)) that protects P19 cells from oxidative damage (M. Kushnir et al. *J Neurochem* 105, 537-545 (2008)), but does not contain the NAP motif (R. Zamostiano et al. *J Biol Chem* 276, 708-714 (2001)).

It was investigated here whether major diseases associated with synaptic dysfunction and microtubule impairment like schizophrenia, exhibit ADNP/ADNP2 transcript deregulation. The results indicate an imbalance in ADNP/ADNP2 expression as a factor impacting disease progression in schizophrenia (a similar and more extensive introduction appears in example 2).

Materials and Methods

Schizophrenia Postmortem Samples

Permission to carry out this study was obtained from the Ethics Committee of the Victorian Institute of Forensic Medicine and the North Western Mental Health Program Behavioral and Psychiatric Research and Ethics Committee. Postmortem hippocampus brain samples from 14 schizophrenia patients and 14 matched normal controls in addition to 12 frontal cortex [Brodmann's area (BA) 9] postmortem samples from schizophrenia patients were obtained from the Rebecca L. Cooper Research Laboratories at the Mental Health Research Institute of Victoria, Australia. The final diagnosis according to DSM-IV criteria was established by consensus by two senior psychiatrists and a psychologist following an extensive case history review using the Diagnostic Instrument for Brain Studies (C. Hill et al., *Am J Psychiatry* 153, 533-537 (1996; S. B. Roberts et al., *Aust N Z J Psychiatry* 32, 73-76 (1998)). Control subjects had no contact with any psychiatric service prior to death, had not received anti-psychotic medication, had not died by suicide or had any neurological disorders. Samples were provided by Professor Galila Again, Ben Gurion University, Israel (Dresner E, Again G, Gozes I. Activity-dependent neuroprotective protein (ADNP) expression level is correlated with the expression of the sister protein ADNP2: Deregulation in schizophrenia. Eur Neuropsychopharmacol 2010 Jul. 1.). The groups were matched by age, sex, postmortem interval (PMI) and pH of brain tissue. The 14 patients, which included 4 women and 10 men, had a mean age of 46.6±15.3 (S.D.) years, a mean duration of illness (DOI) of 17.5±12.4 years, a mean PMI of 43.6±13.4 h and a mean brain pH of 6.3±0.2. The control group included 4 women and 10 men, had a mean age of 46.6±15.4 years, PMI of 42±16.4 h and a mean brain pH of 6.3±0.2. Detailed demographic data of the samples were published elsewhere (Nadri et al., *Schizophr. Res.* 71, 377-382, 2004). All experimental parameters were measured (by E.D.) in a balanced way but blind to diagnosis and demographic data. On completion of all experimental measurements, the diagnostic and demographic data was supplied and all analyses completed.

P19 Cells

Mouse Embryonic teratocarcinoma cells were obtained from the American Type Culture Collection (ATCC, Bethesda, Md.); an initial control batch was a kind gift of Dr. Roi Atlas and Professor Irith Ginzburg, the Weizmann Institute of Science, Rehovot, Israel. P19 cells were grown in minimal essential medium (alpha-MEM) containing 5% fetal calf serum, 100 U/ml penicillin and 0.1 mg/ml streptomycin (Biological Industries, Beit Haemek, Israel) in a 5% $CO_2$ incubator at 37° C. To induce neuronal differentiation, cells were cultivated in 90 mm bacteriological grade dishes and supplemented with 1 µM all-trans retinoic acid (RA, Sigma, St. Louis, Mo., USA) for 4 days as described previously (Akiyama et al. 2003). Cell aggregates were suspended with trypsin-C (Biological Industries) and transferred to poly-L-Lysine (Sigma) coated tissue culture dishes. The cells were grown in RA-free DMEM containing 2.5% fetal calf serum, 4 mM L-glutamine and antibiotics (Biological Industries) for an additional 4 days to induce neuronal and astroglial phenotype. RNA extractions and real-time polymerase chain reaction procedures were performed on the P19 cells before and after RA induced differentiation.

RNA Extraction

Total RNA from controls and schizophrenia patients was purified from brain specimens using Trizol reagent (Sigma) with further purification of the RNA phase by the RNeasy Kit (Qiagen, Hilden, Germany). Purity and concentration of the purified RNA were determined spectrophotometrically (GeneQuant, Pharmacia Biotech, England). RNA from P19 cells was extracted using the RNeasy Plus Mini Kit (Qiagen). The integrity of RNA was determined by fractionation on 1% agarose gel and staining with ethidium bromide. The quantity of RNA was determined by measuring OD260 with a NanoDrop spectrophotometer (NanoDrop Technologies, Wilmington, Del., USA).

Reverse Transcription and Quantitative Real Time PCR

Samples with same amount of total RNA were used to synthesize single-strand cDNA with SuperScript DI RNase H Reverse Transcriptase (Invitrogen, Carlsbad, Calif., USA) and a random hexamers adaptor primer according to the manufacturer's instructions. In each RT-PCR run, two negative controls were included: sterile water to control the purity of the reagents and total RNA without RT enzyme to test genomic contamination. ADNP and ADNP2 expression levels in Schizophrenia were determined using specific primers for human ADNP and ADNP2, and normalized to TATA box binding protein. The endogenous control was chosen so that its expression level will be constant between controls and patients. RNA from non-differentiated and differentiated P19 cells was isolated and the expression of tubulin β3 and glial fibrillary acidic protein (GFAP) was determined to confirm neuronal differentiation. ADNP and ADNP2 expression levels in P19 cells were determined using specific primers for mouse ADNP and ADNP2. Expression of neuronal differentiation markers and of ADNP and ADNP2 were normalized to mouse HPRT1. Primer pairs (table 1) were designed using the primer 3 web interface (http://frodo.wi.mit.edu/primer3/) and synthesized by Sigma-Genosys (The Woodlands, Tex., USA). Real Time PCR was performed using the SYBER GREEN PCR Master Mix and ABI PRISM 7900 Sequence Detection System instrument and software (Applied Biosystems, Foster City, Calif., USA) using the default thermocycler program for all genes: 10 minutes of pre-incubation at 95° C. followed by 40 cycles for 15 seconds at 95° C. and one minute at 60° C. Real-time PCR reactions were carried out in 15 µl volumes in a 96-well plate (Applied Biosystems) containing 7.5 µl of X2 SYBR GREEN PCR Master Mix and ~0.233 nM of each sense and antisense primers. The efficiencies of all primers used were calculated as a precursory step using standard curves, according to the equation: E (efficiency)=$10^{(-1/slope)} - 1 \times 100$ and were near 100% for all primers. All real-time PCR reactions were carried out in triplicate. The comparative Ct method was used for quantification of transcripts. Product specificity was confirmed in the initial experiments by agarose gel electrophoresis and sequencing and routinely by melting curve analysis.

Statistical Analysis

ANOVA with posthoc Fisher's LSD test and Student's t-test were carried out to compare among mean values using the software SPSS. A result of $p<0.05$ (for a 2-tailed distribution) was considered significant. Correlations were analyzed by Pearson's correlation test using SPSS. Comparison between two correlation coefficients was done using the software MedCalc (http://www.medcalc.be/?gclid=CNm699-Fx50CFc8UzAodCmLHvA) and the statistical computation web site, VassarStats (faculty.vassar.edu/lowry/VassarStats.html).

Results

1. ADNP and ADNP2 mRNA Expression Levels are Similar Between Schizophrenia Patients and Controls in Brain Samples In the hippocampus, no difference was detected in the mRNA levels of ADNP or ADNP2 between controls and schizophrenic patients. We decided to omit from the study two samples, one from the control group and the other from the schizophrenia group, in which ADNP2 levels were more than two standard deviation above the mean, although no significant difference between control and schizophrenia ADNP2 levels was found even after these two samples were excluded (table 2). It is important to mention that ADNP and ADNP2 levels were calculated in the comparative Ct method that doesn't allow concluding what was the exact amount of transcript in the sample, thus it is impossible to say that ADNP2 levels are higher than ANDP levels. Hippocampus ADNP and ADNP2 parameters did not correlate with age (r=0.249, p=0.201 for ADNP and r=0.36, p=06 for ADNP2), duration of illness (DOI, r=0.088, p=0.657 for ADNP and r=0.294, p=129 for ADNP2) or pH (r=−0.35, p=0.068 for ADNP and r=−0.28, p=149 for ADNP2) and did not differ between males and females (2±0.6, n=20 vs. 2.2±1.5, n=8, respectively, t=−0.35, p=0.735 for ADNP and 9.2±3.2, n=20 vs. 7.3±6.7, n=8, respectively, t=0.758, p=0.469 for ADNP2). There was no correlation between ADNP and the post-mortem interval (PMI, r=−0.234, p=0.23) but there was a significant correlation between the PMI and ADNP2 (r=−0.388, p=0.041). We checked for interaction affect between diagnosis and PMI, and no such interaction was found ($F_{diagnosis*PMI}(1,24)=0.642$, p=0.431). Thus, we introduced the PMI as a covariate, but no change in ADNP2 levels between controls and schizophrenic patients was detected (F(1,25)=0.04, p=0.844).

2. ADNP2 mRNA Levels are Correlated with Increased Duration of Illness (DOI) in the Schizophrenic Group A correlation between DOI and ADNP2 mRNA levels was observed in the schizophrenia group (r—0.637, p=0.014, n=14, Pearson's correlation). Thus, ADNP2 mRNA levels in patients with DOI>25 years were significantly higher than in the other patients and control (table 3). No other correlations between ADNP2 mRNA levels and other parameters like sex (r=−0.461, p=0.097), age (r=0.455, p=0.102), PMI (r=−0.189, p=0.517) or pH (r=−0.154, p=0.6) in the schizophrenic group were found. In contrast to ADNP2, ADNP mRNA levels did not correlate with DOI.

3. Postmortem Hippocampal ADNP2 mRNA Levels Correlate with Duration of Illness

Figure 1B:
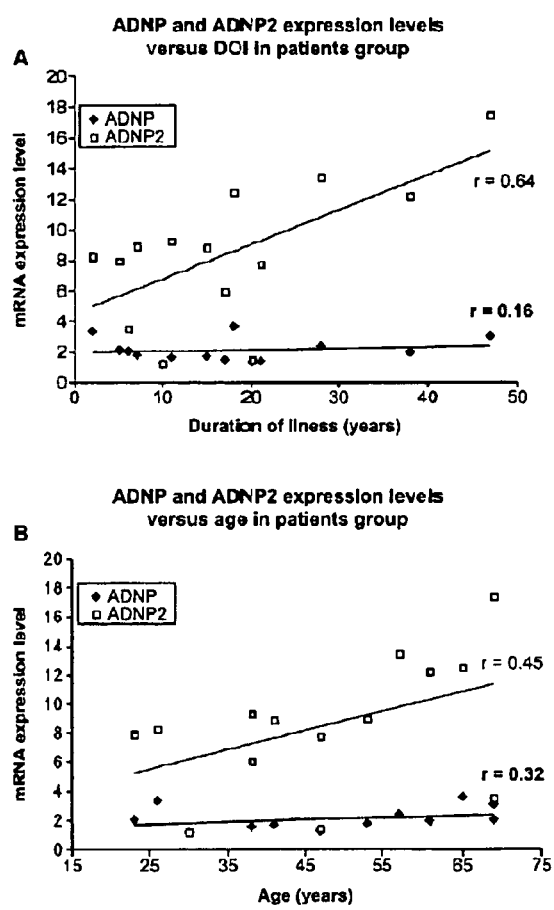

A correlation between DOI and ADNP2 mRNA levels was observed in the schizophrenia patients group (r=0.637, p=0.014, n=14, Pearson's correlation). Importantly, ADNP2 mRNA levels correlated with DOI but not with age (r=0.455, p=0.102). In contrast to ADNP2, ADNP mRNA levels did not correlate either with DOI or with age (FIG. 1). There was no other correlation between ADNP2 mRNA levels and the parameters sex (r=0.461, p=0.097), PMI (r=0.189, p=0.517) or pH (r=0.154, p=0.6) in the schizophrenia patients group.

4. Reduced Correlation Between ADNP and ADNP2 in Schizophrenia Patients

ADNP and ADNP2 belong to the same protein family. The two proteins share 33% identity and 46% similarity and have similar protein domains. Here we found that while high correlation between ADNP and ADNP2 exists in the control group (=0.949, p<0.001, n=14), in the schizophrenia patients this correlation is reduced to r=0.637 (p=0.014, n=14). No other correlation between ADNP or ADNP2 with other parameters was observed (except for ADNP2 and the DOI) in the schizophrenic group, but in the control group there was a significant correlation between ADNP2 levels and the PMI (=−0.562, p=0.036). In order to explore the relationship between ADNP and ADNP2 in the control group, while controlling for the PMI, we used partial correlation test, and found a strong, positive, partial correlation (r=0.931, p<0.001). Inspection of the zero-order correlation (r=0.949) suggested that controlling for the PMI had very little effect on the strength of the relationship between these two variables (FIG. 1). The difference between ADNP and ADNP2 correlation coefficients in the schizophrenic and control group was calculated via VassarStats, statistical computation web site, and via the statistical software MedCalc and was found to be significant (z=2.14, p=0.03). In order to reinforce our finding, we checked the correlation between ADNP and ADNP2 in the men group only, and discovered that while in the control men there was high and significant correlation (r=0.97, p<0.001, n=10), in the schizophrenic men no such correlation existed (r=0.415, p=0.234, n=10).

Figure 2:
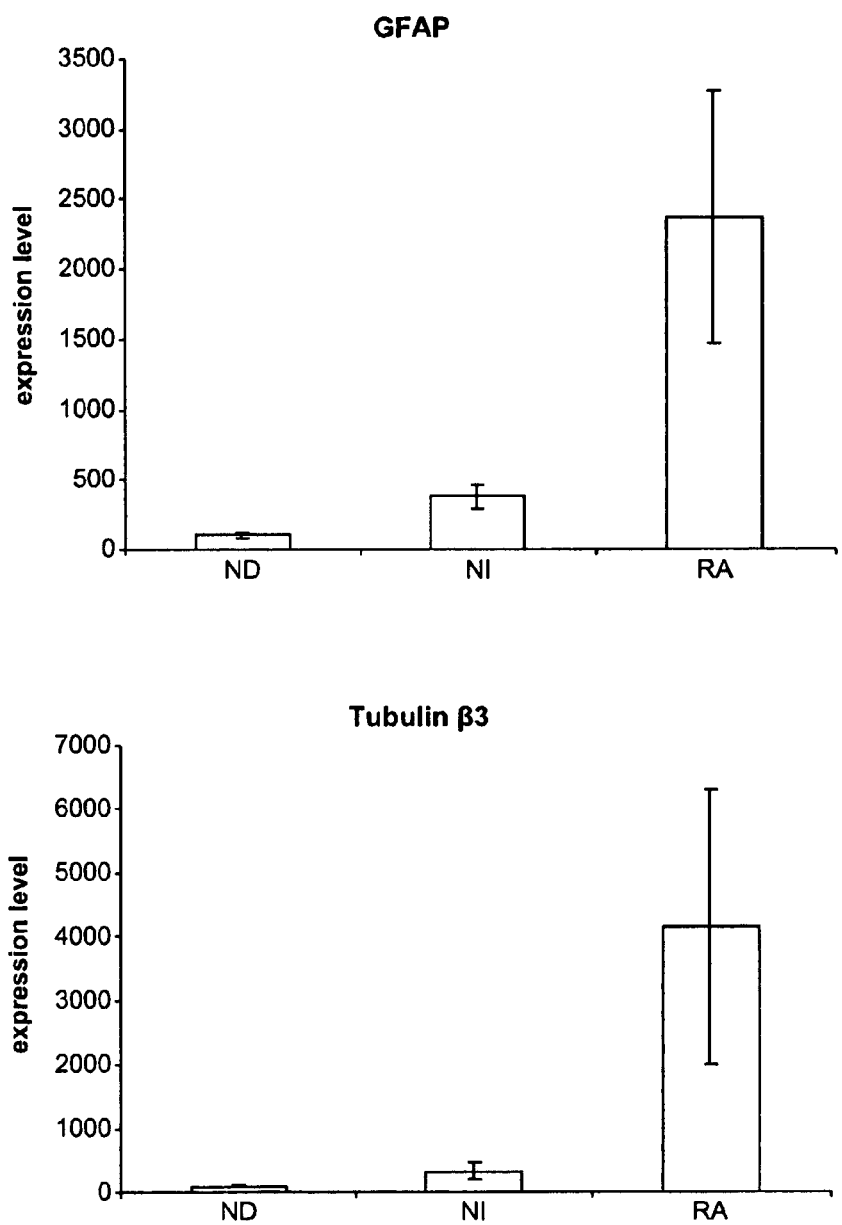
FIG. 2: Differentiated P19 cells express tubulinβ3 (a neuronal marker) and glial fibrillary acidic protein (GFAP) as well as highly correlated expression of ANDP and ADNP2. Eight days after the induction of differentiation, total RNA was extracted and specific differentiation markers were evaluated to validate neuro-differentiation. Real Time PCR analysis was performed analyzing tubulinβ3 and GFAP. Results are from three independent experiments, each one performed in duplicates, and presented in a graphic format as percentage from the ND state (*p<0.05, in comparison to the non-differentiated state). ND=non-differentiated; NI=no inducer; RA=retinoic acid. In the same experiments, ADNP expression was correlated with ADNP2 expression (r=98, p=0.001) (not shown on the figure).

In order to define the importance of ADNP and ADNP2 correlation, we examined whether it is maintained in the P19 model system. P19 cells are pluripotent cells and are originate from mouse embryonic teratocarcinoma. Their embryonic origin and their ability to neurodifferentiate make them an ideal model for studying genes related to CNS functions and pathologies, especially those with developmental aspects, like schizophrenia. RNA was extracted from non-differentiated cells and from cells that were subjected to eight days differentiation process with retinoic acid (RA). In order to ascertain neuro-differentiation, specific markers were evaluated. As controls to the differentiated conditions, both non-differentiated cells as well as cells that went through the differentiation process in the absence of the inducer were evaluated. Q-PCR analysis showed up-regulation of both glial fibrillar acidic protein (GFAP) and tubulinβ3 (glial and neuronal markers, respectively) in the RA treated cells (FIG. 2). Examination of ADNP and ADNP2 correlation showed that in the non differentiated P19 cells the correlation was r=0.999 (p<0.001). The expression level of both ADNP and ADNP2 was increased (data is not shown) in the neuro-differentiated state, yet the high correlation between them was maintained (r=0.98, p=0.001).

Finally, it is worthwhile mention that in the frontal cortex of the same schizophrenia patients there was much higher correlation between ADNP and ADNP2 (r=0.854, p<0.001, n=12) than in the hippocampus, a phenomenon which may reflect differences in ADNP and ADNP2 equilibrium between these two brain regions in schizophrenia.

Discussion

The current example shows for the first time that the expression of ADNP and ADNP2 are highly correlated. Importantly, the correlation of ADNP to ADNP2 expression is dramatically altered in the hippocampus of schizophrenia patients, but not in the cortex, a condition which might reflect differences in ADNP/ADNP2 equilibrium in different brain areas. Either way, these results may indicate the existence of a fine balance between ADNP and ADNP2 expression levels, which is violated in the hippocampus of schizophrenia patients. The hippocampus is an important brain region of neurogenesis in the adult and altered hippocampal neurogenesis may also play a pathophysiological role in neurodegenerative disorders such as Alzheimer's disease and possibly schizophrenia, where psychotropic drug treatment may provide an ameliorative role (J. Hunsberger et al. *Dialogues Clin Neurosci* 11, 333-348 (2009)). During development, ADNP regulates key genes that are associated with neurogenesis such as neurogenin 1 and neurod (S. Mandel et al. *Dev Biol* 303, 814-824 (2007)). As adult neurogenesis has been suggested to be impaired in schizophrenia, it is possible that ADNP/ADNP2 balance is a contributing factor to the progression of the disease (C. T. Toro and J. F. Deakin. *Schizophr Res* 90, 1-14 (2007)). Disease duration can also be associated with extended antipsychotic drug use, which may be a contributing factor to the regulation of ADNP/ADNP2 expression. Antipsychotic drug treatment may cause tauopathy (C. X. Gong et al. *Brain Res* 741, 95-102 (1996)) and as indicated in the Introduction, partial ADNP knockout resulted in tauopathy (I. Vulih-Shultzman et al. *J Pharmacol Exp Ther* 323, 438-449 (2007)), suggesting a possible feedback mechanism in the ADNP/ADNP2 ratio.

Growing evidence connect between cytoskeleton abnormalities and schizophrenia: 1. In the brain, tubulin frameworks are stabilized by stable tubule-only polypeptide (STOP) proteins (C. Bose et al. *Biochemistry* 42, 12125-12132 (2003)) (aka MAP6), a family of MAPs important for cold stable microtubules. Linkages to allelic variation in STOP genes has been reported in schizophrenia, along with altered STOP protein expression in some brain regions (H. Shimizu et al. *Schizophr Res* 84, 244-252 (2006)). STOP-/- mice, exhibit synaptic deficits (A. Andrieux et al. *Genes Dev* 16, 2350-2364 (2002)), disturbances in dopaminergic neurotransmission (P. Brun et al. *J Neurochem* 94, 63-73 (2005)) along with deficits in behavior and hypermotility that are partially reversed with antipsychotic drug treatment (R. L. Fradley et al. *Behav Brain Res* 163, 257-264 (2005)). 2. Alterations in phosphorylation and distribution of the microtubules associated proteins (MAPs) such as MAP2, MAP1B and MAP5 have been found in specific brain areas of schizophrenic patients (S. Doxsey. *Nat. Rev Mol Cell Biol* 2, 688-698 (2001); S. E. Arnold et al. *Proc Natl Acad Sci USA* 88, 10850-10854 (1991)). 3. DISC1 (Disrupted in schizophrenia 1) was found to be associated with schizophrenia, by multiple genetic studies (M. Niethammer et al. *Neuron* 28, 697-711 (2000)). Its protein product is localized at the centrosome, which is the cell's principal microtubule organizing center, regulating the assembly of α and β tubulin into microtubules. When dissociated, microtubules rapidly reassemble from this organelle. Centrosome function, and specifically the cytoplasmic dynein regulator NUDEL, have been implicated in neuronal migration during brain development, because of the centrosomal regulation of microtubules, and NUDEL binding to LIS1, which is required for normal cerebral cortical histogenesis (T. D. Cannon et al. *Arch Gen Psychiatry* 62, 1205-1213 (2005); R. J. Leventer et al. *Trends Neurosci* 24, 489-492 (2001)). Disruption of these centrosomal/NUDEL functions by loss of DISC1 association may produce developmental and neurite architecture abnormalities, such as have been reported in schizophrenia (M. A. Hayashi et al. *Proc Natl Acad Sci USA* 102, 3828-3833 (2005); R. W. Buchanan and W. T. Carpenter, Jr. *Schizophr Bull* 23, 367-372 (1997)). Using immunocytochemical and biochemical approaches, Morris et al. observed robust physical interaction between DISC1 and the microtubule-associated proteins MIPT3 and MAP1A. Yeast two-hybrid experiment also identified microtubules associated protein 1A (MAP1A) as interacting with the N-terminus of DISC1. MAP1A is a microtubule associated protein which stabilizes microtubules and is expressed predominantly in mature neurons (J. A. Morris et al. *Hum Mol Genet*. 12, 1591-1608 (2003)). As discussed above, ADNP and NAP interact with microtubules, which are impaired in schizophrenia—thus positioning ADNP as a possible player in the patophysiology of the disease.

ADNP2 has been assigned to chromosome 18q23 as we described before (M. Kushnir et al. *J Neurochem* 105, 537-545 (2008)) and linkage analysis suggest that this region is associated with bipolar disorder (C. Van Broeckhoven and G. Verheyen. *Am J Med Genet*. 88, 263-270 (1999)). Together with our current data, it is suggestive that gene expression homeostasis is important in these multifactorial disease.

Importantly, the change in ADNP/ADNP2 balance with increase in ADNP2 that lacks the neuroprotective NAP motif (R. Zamostiano et al. *J Biol Chem* 276, 708-714 (2001)) suggests hope for treatment of schizophrenic patients with NAP. NAP is currently under clinical development (generic name, davunetide) by Allon Therapeutic Inc. (website: allontherapeutics) and has shown cognitive protection in patients suffering from amnestic mild cognitive impairment (I. Gozes et al., 2009, *Curr Alzheimer Res* 6:455-460) and improved daily activities in schizophrenic patients (D. C. Javitt Schizophrenia Research 2010; 117, 118-9).

TABLE 1

Primers sequences

| Primer | Sequence |
|---|---|
| Human ADNP (NM_015339) | 5' acttacgaaaaaccaggactatc 3' |
|  | 5' gacattgcggaaatgac 3' |
| Human ADNP2 (NM_014913) | 5' gaaagaaagtgagatatcgaacaaa 3' |
|  | 5' tggtcaatttcatcttcatgg 3' |
| Human TATA box binding protein (NM_003194) | 5' ggagccaagagtgaagaacag 3' |
|  | 5' cacagctccccaccatattc 3' |
| Mouse Tubulin β3 (NM_023279) | 5' aactttatctttggtcagagtggt 3' |
|  | 5' tgcaggcagtcacaattctc 3' |
| Mouse Glial fibrillary acidic protein (GFAP) (NM_001131020) | 5' gaaaccgcatcaccattc 3' |
|  | 5' ccttctgacacggatttggt 3' |
| Mouse ADNP (NM_009628) | 5' acgaaaaatcaggactatcgg 3' |
|  | 5' ggacattccggaaatgacttt 3' |
| Mouse ADNP2 (NM_175028) | 5' ggaaagaaagcgagataccg 3' |
|  | 5' tcctggtcagcctcatcttc 3' |
| Mouse HPRT1 (NM_013556) | 5' ggatttgaatcacgtttgtgtc 3' |
|  | 5' caggactcctcgtatttgcag 3' |

TABLE 2

Postmortem hippocampus ADNP and ADNP2 mRNA levels of schizophrenic patients vs. controls

| | Schizophrenia | | Control | |
|---|---|---|---|---|
| | N | mean ± S.D | N | mean ± S.D |
| ADNP mRNA levels, arbitrary units | 14 | 2.1 ± 0.76 | 14 | 2 ± 1.1[a] |

TABLE 2-continued

Postmortem hippocampus ADNP and ADNP2 mRNA levels of schizophrenic patients vs. controls

| | Schizophrenia | | Control | |
|---|---|---|---|---|
| | N | mean ± S.D | N | mean ± S.D |
| ADNP2 mRNA levels, arbitrary units | 14 | 8.5 ± 4.5 | 14 | 8.9 ± 4.4[b] |

[a]t-test: t = 3.153, p = 0.88.
[b]t-test: t = −0.209, p = 0.836.

TABLE 3

Increased ADNP2 mRNA levels in schizophrenia patients with DOI ≥ 25

| | | schizophrenia | |
|---|---|---|---|
| | Control | DOI < 25 years | DOI ≥ 25 years |
| N | 14 | 11 | 3 |
| Age (years, mean ± SD) | 45.9 ± 15.7 | 43.4 ± 14.8 | 62.3 ± 6.1[a] |
| ADNP2 mRNA levels, (arbitrary units, mean ± SD) | 8.8 ± 4.4 | 6.9 ± 3.5 | 14.4 ± 2.7[b] |

[a]ANOVA: F = 1.978, df = 2.25, p = 0.159.
[b]ANOVA: F = 4.215, df = 2.25, p = 0.026; post-hoc LSD: p = 0.038 from controls and p = 0.008 from schizophrenia patients with DOI < 25 years.

Example 2

A Diagnostic Kit Based on ADNP/ADNP2 Expression Ratio

Activity-Dependent Neuroprotective Protein (ADNP): Regulation of Gene Expression ADNP (I. Gozes. Pharmacol Ther 114, 146-154 (2007)) is suggested to be a transcription factor containing a homeobox domain profile with sequence motifs that are associated with nuclear localization as well as cellular secretion and uptake. These structural characteristics imply nuclear, cytoplasmic and extracellular functions (R. Zamostiano et al. J Biol Chem 276, 708-714 (2001); M. Bassan et al. J Neurochem 72, 1283-1293 (1999)). Genetic manipulation and complete knockout of ADNP in the mouse, revealed cranial neural tube closure failure and death on E8.5-9.0 of the ADNP-knockout embryos (A. Pinhasov et al. Brain Res Dev Brain Res 144, 83-90 (2003)). The expression of Oct4, a gene associated with germ-line maintenance was markedly augmented in the knockout embryos. In contrast, the expression of Pax6, a gene crucial for cerebral cortex formation, was abolished in the brain primordial tissue of the knockout embryos. Thus, Pax6 and Oct4 constitute a part of the mechanism of action of ADNP on brain formation, inhibiting germ-line division while activating morphogenesis (A. Pinhasov et al. Brain Res Dev Brain Res 144, 83-90 (2003)). As indicated above (example 1), to further elucidate ADNP associated pathways, Affymetrix microarrays were used on ADNP knockout and control mouse embryos (E9) showing changes in >400 genes. A group of dramatically up-regulated gene transcripts in the ADNP-deficient embryos were clustered into a family encoding for proteins enriched in the visceral endoderm such as apolipoproteins, cathepsins and methallotionins. A down regulated gene cluster associated with ADNP-deficiency in the developing embryo consisted of organogenesis markers including neurogenesis (Ngfr, neurogenin1, neurod1) and heart development (Myl2) (S. Mandel et al. Dev Biol 303, 814-824 (2007)). These results place ADNP at a crucial point of gene regulation, repressing potential endoderm genes and enhancing genes associated with organogenesis/neurogenesis. Immunoprecipitation experiments showed interactions with heterochromatin protein1α (HP1α) (S. Mandel et al. Dev Biol 303, 814-824 (2007)) and with BRG1, BAF250a, and BAF170, all components of the SWI/SNF (mating type switching/sucrose nonfermenting) chromatin remodeling complex (S. Mandel and I. Gozes. J Biol Chem 282, 34448-34456 (2007)). Together, these results place ADNP in a chromatin remodeling epigenetic role in neurodifferentiation and neuroplasticity.

In the adult, ADNP mRNA expression was observed in the mouse brain and in the human brain with high concentrations in the cerebellum, hippocampus and cerebral cortex (R. Zamostiano et al. J Biol Chem 276, 708-714 (2001); M. Bassan et al. J Neurochem 72, 1283-1293 (1999)). Comparable amounts of ADNP mRNA were identified in the mouse and the human spleen (R. Zamostiano et al. J Biol Chem 276, 708-714 (2001); M. Bassan et al. J Neurochem 72, 1283-1293 (1999)) and further studies identified ADNP expression in macrophages (F. J. Quintana et al. Ann N Y Acad Sci 1070, 500-506 (2006)).

ADNP Gene Expression is Regulated by Immune Status and Injury

Comparative analysis of ADNP mRNA in peripheral blood mononuclear cells (PBMCs, i.e., T cells, B cells, monocytes and natural killer cells) of normal subjects (N=21) and multiple sclerosis (MS, N=24) patients showed that monocytes, B cells and T cells, but not regulatory (CD4+CD25+) T cells expressed ADNP. ADNP mRNA which was reduced in the PBMCs of MS patients compared to those of the healthy controls (M. Braitch et al. Neuroimmunomodulation 17, 120-125 (2009)).

Up-regulation of ADNP mRNA expression as well as ADNP-like immunoreactivity has also been suggested to occur in activated microglial cells one month following injury since strong glial expression was found following traumatic brain injury in mice (I. Gozes et al. Curr Alzheimer Res 2, 149-153 (2005); R. Zaltzman et al. J Mol Neurosci 24, 181-187 (2004)). Additional studies suggested only infrequent ADNP staining of glial cells in normal adult rodent brain and it was further hypothesized that ADNP may be activated to a nuclear binding capacity in stressed or injured cells (N. Gennet et al. Histol Histopathol 23, 309-317 (2008)). It is thus possible that ADNP expression and localization is regulated by injury. Other potential regulators of ADNP expression include vasoactive intestinal peptide (VIP) (S. Furman et al. Neuron Glia Biology 1, 193-199 (2004)) and pituitary adenylate cyclase activating polypeptide (PACAP) nerve growth factor (NGF) (T. Thippeswamy et al. J Mol Neurosci 33, 268-277 (2007)) and the NO-cGMP pathway (A. S. Cosgrave et al. J Mol Neurosci (2009); A. S. Cosgrave et al. Neurobiol Dis 30, 281-292 (2008)); all associated with neuroplasticity and neuroprotection. Interestingly, in the arcuate nucleus, a region exhibiting brain plasticity in the adult, ADNP expression has shown sexual dichotomy and changes with the estrous cycle, suggesting regulation by sex hormones (see also D. Dangoor et al. Peptides 26, 2579-2584 (2005)) and an involvement with neuronal plasticity (S. Furman et al. Neurosci Lett 373, 73-78 (2005)).

Furthermore, xenon and other inhalational agents induce cell and organ protection through different and only partially elucidated molecular mechanisms. Anesthesia induced or pharmacologic preconditioning is a recognized mechanism of cell protection. In a recent study, changes in ADNP expression in neonatal rat brain as consequence to xenon exposure, compared the noble gas to nitrogen was studied. Seven-day-old Sprague Dawley rats were exposed for 120 min to 75% xenon and 25% oxygen or control condition consisting of 75% nitrogen and 25% oxygen (Air). ADNP was found to be differentially expressed as validated by Relative Real-Time PCR(RT-PCR) and confirmed by western blot and immunohistochemistry. The differential expression of ADNP in the rat neonatal brain may account for the preconditioning and neuroprotective effects exerted by gas xenon (D. Cattano et al. *Neurosci Lett* 440, 217-221 (2008)).

Neuroglial Interaction

Original ADNP-like immunoreactive localization studies were performed in rat primary astrocytes showing ADNP-immunostaining in the nucleus, cytoplasm and extracellular milieu. In the cytoplasm, occasional co-localization in the vicinity of microtubules was observed and in the extracellular milieu (S. Furman et al. *Neuron Glia Biology.* 1, 193-199 (2004)). Partial deficiency in ADNP as a consequence of genetic manipulations (I. Vulih-Shultzman et al. *J Pharmacol Exp Ther* 323, 438-449 (2007)) or alcohol toxicity (M. Pascual and C. Guerri. *J Neurochem* 103, 557-568 (2007) was associated with reduced capacity of astroglial cells to provide neuroprotection (I. Vulih-Shultzman et al. *J Pharmacol Exp Ther* 323, 438-449 (2007)) and neurotrophic functions (M. Pascual and C. Guerri. *J Neurochem* 103, 557-568 (2007)).

In neuronal-like cell lines, ADNP short hairpin RNA down-regulation resulted in microtubule reorganization and changes in cell morphology including reduction in cell process formation [as measured by staining of the microtubule associated protein (MAP2)], reduction in cell number was also associated with ADNP knockdown. These morphological changes are closely associated with the SWI/SNF complex multifunctionality on the one hand and may also imply a cytoplasmic function (S. Mandel et al. *J Mol Neurosci* 35, 127-141 (2008)).

Tauopathy and Alzheimer's Disease Pathology

While complete ADNP-deficiency is lethal, ADNP heterozygous mice (+/−) survive, but exhibit phenotypic deficiencies. ADNP+/− male mice exhibited cognitive deficits, significant increases in phosphorylated tau, tangle-like structures emanating from astrocytes (as described for tauopathies like corticobasal degeneration and progressive supranuclear palsy) and neurodegeneration (cell death) as compared to ADNP+/+ mice (I. Vulih-Shultzman et al. *J Pharmacol Exp Ther* 323, 438-449 (2007)).

Interestingly, studies in other laboratories indicated that deletions in the human ADNP chromosomal region (20q12-13.2, R. Zamostiano et al. *J Biol Chem* 276, 708-714 (2001)) may be associated with mental retardation in man (W. Borozdin et al. *Hum Mutat* 28,830 (2007)).

To test whether ADNP is affected by the onset of Alzheimer's disease (AD) pathology and progression, the PS1×APP mouse model (PS1$_{M146L}$×APP$_{751SL}$ tg mice) was employed to analyze the mRNA expression of ADNP in the hippocampus and cerebellum in early and advanced stages of disease. Results showed that ADNP expression in 6-month-old PS1×APP mice hippocampus was higher than in wild type (WT) mice. ADNP was originally identified as a VIP-responsive gene taking part in the VIP-mediated neurotrophic pathway. Interestingly, the expression of VIP was not affected in the same experimental setting, suggesting that ADNP expression is a VIP-independent marker associated with AD. Moreover, in the cerebellum, a brain area not affected by Aβ deposition, both ADNP and VIP mRNA expression in 6-months-old PS1×APP and WT were not different. A similar extent of hippocampal ADNP expression was observed in 18-month-old WT and PS1×APP mice, in contrast to the differential expression level at 6 months of age. However, hippocampal ADNP expression in both WT and PS1×APP was increased with aging similar to VIP mRNA expression. These findings support the hypothesis that ADNP expression is related to early/mild AD progression by a VIP-independent mechanism (R. Fernandez-Montesinos et al. *J Mol Neurosci* (2010) 41:114-120).

Figure 3A:
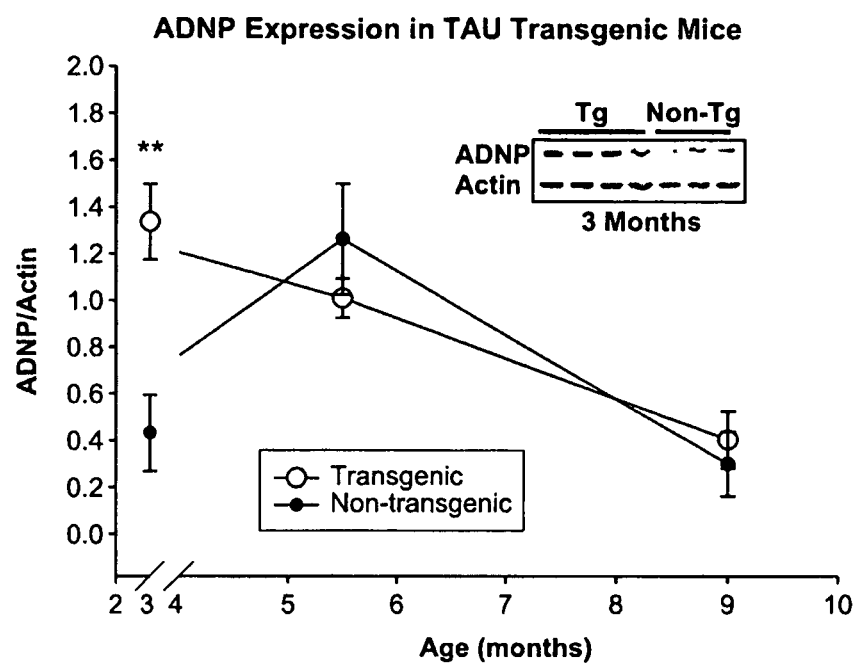
FIG. 3: A. ADNP expression is correlated with tauopathy and aging. Nuclear ADNP expression was assessed using mouse monoclonal antibody directed against ADNP (1:300 dilution; BD Bioscience) at 150 KD, actin was used as a control. Expression of nuclear ADNP in the cortex of 3-month-old transgenic mice in comparison of non-transgenic littermates is shown by gel electrophoresis, quantitative western blots, and quantitative densitometry (Tg=transgenic, Non-tg=wildtype littermates, **P<0.01). B. a dramatic increase in ADNP expression in the tau transgenic young mice, which is decreased and leveled off as the mice mature and age. This is correlated with protein expression and with tau 3R expression. C. Western blot showing reduced expression of transgene, ADNP, and tau3R in mice after doxycycline treatment. Tau expression was measured in the cytoplasmic fraction; ADNP was measured in nuclear fractions. D. Western blots showing expression level of ADNP in transgenic and non-transgenic mice after doxycycline treatment.

Similarly, in a model of "pure" tauopathy (Ramsden et al. *J Neurosci* 25, 10637-10647 (2005)), the rTg(tau(P301L)) 4510 mouse expressing the P301L mutation in tau (4R0N) associated with frontotemporal dementia and parkinsonism linked to chromosome 17 in the cerebral cortex and hippocampus and in which memory loss and pre-tangle pathology appears already at the age of 2.5 months, preliminary results (FIG. 3A) show an increase in ADNP immunoreactivity in the nuclear fraction (prepared as in S. Goldberg et al. *J Neurochem* 111, 72-79 (2009)) obtained from 3-month-old mice (cerebral cortex tissue). In contrast, at 5.5 months there were similar amounts of ADNP (with an apparent increase in the control mice and an apparent decrease in the transgenic mice compared to 3-month-old mice and the decrease continued at 9 months of age (FIG. 3A).

In the same tauopathy model (Ramsden et al., supra), ADNP mRNA expression correlated with the dynamic 3R tau mRNA expression, corroborating the observation for increases in 3R tau expression probably in compensation for the 4R tau transgene expression.

Figure 3B:
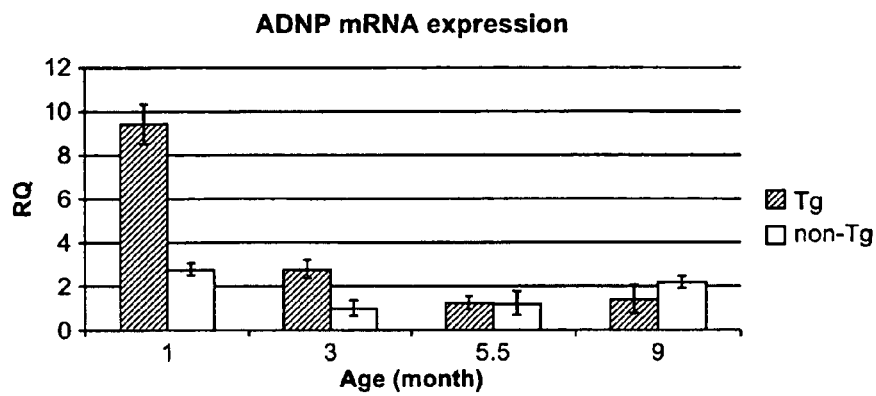

Messenger RNA levels of ADNP and tau 3R in Tg and non-Tg mice (1, 3, 5.5, 9 month-old) were obtained by quantitative real time RT-PCR. RNA was isolated using MasterPure™ RNA Purification Kit (Epicentre Biotechnologies, USA). Total RNA was subjected to reverse transcription (RT) using high-capacity cDNA reverse transcription kit (Applied Biosystems, Foster City, Calif.). Real time PCR was performed using powered SYBR green PCR master kit (Applied Biosystems) and ABI PRISM 7900 sequence detection system instrument and software (Applied Biosystems). Hypoxanthine-guanine phosphoribosyltransferase (HPRT) was used as the normalization control gene. Relative levels to HPRT (RQ) are shown in FIG. 3B.

The changes in ADNP expression parallel changes in tau 3R expression. Tau 3R expression has been shown before to be regulated in the model as describe in Dickey C et al., *Am J Pathol* 174: 228-238, 2009. Novel findings described here show a correlation with ADNP expression. Relative levels to HPRT (RQ) are shown here.

Figure 3C:
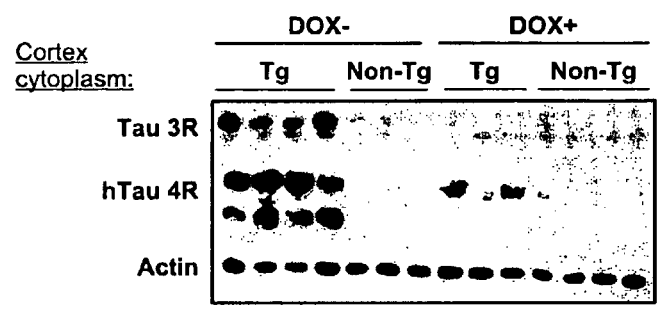

The advantage of the above model is the ability to shut down the transgene by doxycycline treatment as follows in Ramsden et al., supra. 2-month-old mice were treated with doxycycline for three weeks resulting in transgene shutoff and a reduction in ADNP is also seen as well as in tau 3R expression as analyzed by western blots (FIG. 3C). hTau 4R is the transgene that is dramatically down-regulated by doxycycline as expected.

Figure 3D:
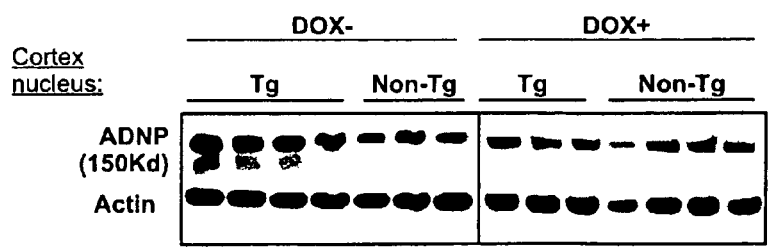

The fact that our results also indicated a reduction in ADNP expression following transgene shutdown indicates a reciprocal relation between ADNP expression levels and tau splicing. Thus, the ADNP protein expression ratio between the Tg and non-Tg mice is 3 and between the Tg and non-Tg treated with doxycycline is 1. See FIG. 3D.

Thus, ADNP undergoes differential changes in a model of taouopathy showing increase in the young age at the pre-tangle stage and a marked decrease with aging and degeneration. The question is if these results are reflected in blood samples of the human patient, which will place ADNP as a surrogate diagnostic tool for early diagnosis and disease progression while corroborating the need for ADNP-like replacement therapy.

ADNP-NAP Replacement Therapy

Our original results suggested that recombinant ADNP provides potent protection against severe oxidative stress as well as against Aβ toxicity in cell cultures (R. A. Steingart and I. Gozes. *Mol Cell Endocrinol* 252, 148-153 (2006)). As ADNP is a large protein with potentially limited bioavailability, peptide activity scan was performed and our research demonstrated that an 8-amino-acid peptide fragment of ADNP, NAP was capable of conferring neuroprotection (M. Bassan et al. *J Neurochem* 72, 1283-1293 (1999)) and neurotrophic activity (I. Gozes and I. Spivak-Pohis. *Curr Alzheimer Res* 3, 197-199 (2006)). NAP, formulated for intranasal, intravenous, and subcutaneous administration (I. Gozes et al. *CNS Drug Rev* 11, 353-368 (2005)), has the following amino acid sequence: Asn-Ala-Pro-Val-Ser-Ile-Pro-Gln (NAPVSIPQ) (M. Bassan et al. *J Neurochem* 72, 1283-1293 (1999)). NAP was identified as a potent neuroprotectant in a range of in vitro models (I. Gozes et al. *CNS Drug Reviews* 11, 363-378 (2005)) against a number of toxic insults including several relevant to neurodegenerative diseases such as amyloid beta peptides (I. Gozes et al. *BMC neuroscience* 9 Suppl 3,S3 (2008); M. Bassan et al. *J Neurochem* 72, 1283-1293 (1999)), excitotoxicity (M. Bassan et al. *J Neurochem* 72, 1283-1293 (1999)), and oxidative stress (R. A. Steingart et al. *J Mol Neurosci* 15, 137-145 (2000)). Further experiments identified NAP as a neurotrophic factor, stimulating neurite and synapse formation (V. L. Smith-Swintosky et al. *J Mol Neurosci* 25, 225-238 (2005)). To understand the biological significance of NAP activity, mice deficient of the NAP-containing protein, ADNP have been formed. As indicated, while the complete ADNP knockout embryos do not form a brain and die in utero (A. Pinhasov et al. *Brain Res Dev Brain Res* 144, 83-90 (2003); S. Mandel et al. *Dev Biol* 303, 814-824 (2007)), the heterozygous mice live and exhibit severe learning deficiencies which are ameliorated, in part, by intranasal NAP treatment (I. Vulih-Shultzman et al. *J Pharmacol Exp Ther* 323, 438-449 (2007)). Tau hyperphosphorylation occurs in these ADNP deficient mice and is reduced with NAP treatment (I. Vulih-Shultzman et al. *J Pharmacol Exp Ther* 323, 438-449 (2007)), demonstrating functionally significant role for ADNP/NAP in limiting tau hyperphosphorylation. NAP has been shown to be active in a number of transgenic mouse models of dementia including AD and tau mutations. For instance, it reduced neurofibrillary tangle-like structures "NFTs" and tau hyperphosphorylation in a "pure" tauopathy model that has direct relevance of fronto-temporal dementia (N. Shiryaev et al. *Neurobiol Dis* 34, 381-388 (2009)). These double transgenic mice have two mutant tau transgenes (P301S; K257T) under the control of the tau promoter. The mice develop inclusions in the hippocampus and cortex accompanied by cognitive and behavioral dysfunction. Daily treatment of the tau transgenic mice with intranasal NAP over several months reduced tau phosphorylation and "NFTs" while improving short-term memory (N. Shiryaev et al. *Neurobiol Dis* 34, 381-388 (2009)). Thus, long-term NAP treatment associated with reduction in tau pathology may improve cognitive function and slow disease progression. The triple transgenic mouse model of AD expressing mutant APP (Swedish), tau (P301L), and presenilin-1 (M146V) develops both NFTs and amyloid beta plaques in a progressive fashion (S. Oddo et al. *Neuron* 39, 409-421 (2003)). Treatment of 12-month-old mice with an intranasal dose of ~0.07 mg/kg/day for 3 months resulted in a 70% decrease in phosphorylated tau at Ser202/Thr205 and Thr231 residues (Y. Matsuoka et al. *J Mol Neurosci* 31, 165-170 (2007); Y. Matsuoka et al. *J Pharmacol Exp Ther* 325, 146-153 (2008)). Histological examination of the hippocampal CA1 region confirmed that NAP treatment resulted in a reduction of phosphorylated tau. Treatment of 9-month-old animals with an intranasal dose of ~0.017 mg/kg/day for 3 months resulted in a 30% to 40% decrease in phosphorylated tau.

Importantly, in the mouse model of partial ADNP deficiency (ADNP+/− mice), NAP treatment (0.5 µg/mouse/day) partially ameliorated cognitive deficits and reduced tau hyperphosphorylation. Furthermore, NAP treatment reduced the amount of active GSK-3β (I. Vulih-Shultzman et al. *J Pharmacol Exp Ther* 323, 438-449 (2007)), a key enzyme associated with tau hyperphosphorylation (among other activities).

NAP treatment corrected ADNP deficiency in other systems as well. In short, alcohol exposure causes changes in ADNP expression (S. H. Poggi et al. *Am J Obstet Gynecol* 189, 790-793 (2003)). A reduction in the ADNP mRNA levels in the cerebral cortex and astrocytes from prenatal ethanol exposed (PEE) fetuses was observed (M. Pascual and C. Guerri. *J Neurochem* 103, 557-568 (2007)) and it was proposed that some ethanol effects on brain development and synaptic formation are, in part, mediated by the ethanol-induced impairment of the synthesis and release of ADNP by astroglial cells (M. Pascual and C. Guerri. *J Neurochem* 103, 557-568 (2007)). Cortical neurons co-cultured with PEE astrocytes presented a reduction in the dendrite number and shorter dendritic branching than neuron-control glia co-cultures. In this system, NAP significantly increased dendritic and axonal growth or branching as well as the density of the synaptic structures as stained by SNAP-25 and synaptophysin. NAP treatment significantly stimulated the activity of ERK (externally regulated kinase) and Akt in a time-dependent manner in this system. Furthermore, NAP treatment resulted in an increase in CREB phosphorylation, which is known to be a downstream target of the MAPK/ERK and PI-3K/Akt pathways stimulated by growth factors in neurons. CREB is an important transcription factor and accumulating data suggests that patterns of transcription regulation represent the molecular signatures of long-term synaptic changes and memory formation (C. M. Alberini. *Physiol Rev* 89, 121-145 (2009)), implicating NAP activity in memory processes associated with transcriptional regulation.

As indicated above, complete ADNP knockout in mice resulted in cranial neural tube closure failure and death on E8.5-9.0 (A. Pinhasov et al. *Brain Res Dev Brain Res* 144, 83-90 (2003)). In other studies, ethanol addition to gestational day 8.0 mouse embryos resulted in neural tube defects (NTDs) consistent with total dysraphia and anencephaly. Co-incubation with ethanol and NAP significantly increased the percentage of embryos that had begun to close their neural folds at the level of the forebrain/midbrain junction or that had progressed beyond this stage of closure (S. Y. Chen et al. *Dev Neurosci* 27, 13-19 (2005)). In vivo, NAP treatment protected against alcohol-induced serotonergic loss during brain development (around the time of neural tube closure) in the caudal raphe (F. C. Zhou et al. *Alcohol Clin Exp Res* 32, 1361-1371 (2008)). These findings were extended to show that NAP potentiated axon outgrowth in cerebellar granule neurons by activating the sequential tyrosine phosphorylation of Fyn kinase and the scaffold protein Crk-associated substrate (Cas). Pharmacological inhibition of Fyn kinase or expression of a Fyn kinase siRNA abolished NAP-mediated axon outgrowth. Concentrations of ethanol attained after social drinking blocked NAP-mediated axon outgrowth (IC(50)=17 mM) by inhibiting NAP activation of Fyn kinase and Cas (S. Chen and M. E. Charness. *Proc Natl Acad Sci USA* (2008)). These studies tie in with the in vitro studies described above, as Fyn kinase is associated with the Akt and ERK pathways protecting against oxidative stress (M. K. Hwang et al. *Biochem Pharmacol* 77, 1213-1222 (2009)).

In humans, intranasal NAP (generic name, davunetide) has been studied for the treatment of amnestic MCI. The study was a randomized, double-blind, placebo-controlled, parallel group study. The effect of 5 mg once daily and 15 mg twice daily compared to placebo was evaluated in several tests of cognitive function. 144 subjects were randomized and 125 subjects completed the study. Subjects treated with 15 mg twice daily demonstrated a general pattern of improvement in cognitive tests that primarily assessed attention and working memory function. Both doses of NAP were safe and well tolerated. Headache and nasopharyngeal symptoms were the most commonly reported adverse events (I. Oozes et al. *Curr Alzheimer Res* 6 (2009)).

NAP Therapeutic Advantages in Other Microtubule-Deficient Systems: Schizophrenia-Associated Cognitive Dysfunction A recent study was set out to investigate whether a mouse model of schizophrenia that is associated with cytoskeletal deficits exhibited cognitive deficits and whether chronic intranasal NAP treatment was effective in cognitive enhancement in this model. The stable tubule-only polypeptide (STOP) knockout mice have been shown before to provide a reliable model for schizophrenia. In an original study, heterozygous STOP mice (STOP+/−) showed schizophrenia-like symptoms (hyperactivity in open field and cognitive dysfunction, in a test of object recognition/discrimination) that were ameliorated by chronic treatment with clozapine (a clinically used anti-psychotic drug). Following model validation, STOP+/− mice were subjected to daily nasal NAP or vehicle application and compared to similarly treated STOP+/+ mice. NAP treatment significantly decreased open field locomotor activity in the STOP+/− mice. Importantly, STOP+/− mice were significantly impaired in object recognition and were significantly improved to STOP+/+ performance level upon NAP treatment. Finally, spatial memory was also impaired in the STOP+/− mice and was ameliorated by NAP treatment. These studies provide support for further clinical testing of NAP (generic name, davunetide, intranasal formulation—AL-108) on cognitive functions in schizophrenic patients (A. Merenlender-Wagner et al. *J Mol Neurosci* 39 S89 (2009), Peptides 2010; 31:1368-73).

In general, studies to evaluate the mechanism of action of NAP suggest interaction with tubulin (I. Divinski et al. *J Biol Chem* 279, 28531-28538 (2004)), reorganization of microtubular structures in astrocytes and neurons (I. Divinski et al. *J Biol Chem* 279, 28531-28538 (2004); I. Divinski et al. *J Neurochem* 98, 973-984 (2006)) and inhibition of increases in phosphorylated tau (I. Gozes and I. Divinski. *J Alzheimers Dis* 6,S37-41 (2004)). Importantly, treatment of astrocytes or neurons with zinc chloride resulted in tubulin zinc sheet formation and cell death that was protected by the addition of NAP (I. Divinski et al. *J Biol Chem* 279, 28531-28538 (2004); I. Divinski et al. *J Neurochem* 98, 973-984 (2006)). Additionally, NAP reversed microtubule depolymerization by nocodazole in neurons (I. Divinski et al. *J Biol Chem* 279, 28531-28538 (2004); I. Divinski et al. *J Neurochem* 98, 973-984 (2006)).

As already eluded to above, NAP induced neurite outgrowth in primary neuronal cell cultures and in neuronal models (I. Gozes and I. Spivak-Pohis. *Curr Alzheimer Res* 3, 197-199 (2006); W. A. Lagreze et al. *Invest Ophthalmol Vis Sci* 46, 933-938 (2005; V. L. Smith-Swintosky et al. *J Mol Neurosci* 25, 225-238 (2005); I. Divinski et al. *J Neurochem* 98, 973-984 (2006; L. Visochek et al. *J Neurosci* 25, 7420-7428 (2005)). Neurite outgrowth is a process dependent on slow microtubule transport and intact microtubular system.

Screening NAP on receptor panels did not reveal any significant binding to known cell surface receptors. Fluorescent NAP was found inside cells, in the vicinity of microtubules when it was incubated with cells at 4° C. and at low pH (conditions that exclude receptor-mediated endocytocis) (I. Divinski et al. *J Biol Chem* 279, 28531-28538 (2004)). Furthermore, NAP activity is independent of its chirality (D. E. Brenneman et al. *J Pharmacol Exp Ther* 309, 1190-1197 (2004)) and NAP shares sequence similarities with protein sequences that have membrane permeability properties (I. Divinski et al. *J Biol Chem* 279, 28531-28538 (2004)). Taken together, the data suggests an intracellular target for NAP.

β-tubulin interacts with NAP affinity columns and paclitaxel (a microtubule stabilizing agent that interacts with β-tubulin) reduced NAP-tubulin interaction (I. Divinski et al. *J Neurochem* 98, 973-984 (2006)). The importance of this interaction in NAP's effects in on microtubules is currently being investigated. Interestingly, NAP, unlike paclitaxel, does not affect cancer cell division (I. Gozes et al. *J Mol Neurosci* 20, 315-322 (2003)).

Our original comparative sequences analyses identified an ADNP paralog (33% identity and 46% similarity), and indicated that these two genes (ADNP and ADNP2) belong to a novel protein family with a nine-zinc finger motif followed by a homeobox domain, R. Zamostiano et al. *J Biol Chem* 276, 708-714 (2001). ADNP2 has been assigned to chromosome 18q23 as we described before (M. Kushnir et al. *J Neurochem* 105, 537-545 (2008)), and linkage analysis suggest that this region is associated with bipolar disorder (C. Van Broeckhoven and G. Verheyen *Am J Med Genet.* 88, 263-270 (1999)). To gain insight into ADNP2 function, ADNP2-deficient cell lines were established by the RNA silencing (small interfering RNA) technology. ADNP2 deficiency significantly changed the toxicity induced by hydrogen peroxide in P19 embryonic carcinoma cells, similar to what would be predicted for ADNP deficiency. These findings suggest that this gene product may have an important function in brain by playing a role in cellular survival pathways (M. Kushnir et al. *J Neurochem* 105, 537-545 (2008)).

NAP is currently under clinical development (generic name, davunetide) by Allon Therapeutic Inc. (website: allontherapeutics) and has shown cognitive protection in patients suffering from amnestic mild cognitive impairment (I. Gozes et al. *Curr Alzheimer Res* 6, 455-460 (2009)) (above) and improved daily activities in schizophrenic patients (D. C. Javitt Schizophrenia Research 2010; 117, 118-9). Thus, in humans, a randomized, double-blind, placebo-controlled, parallel group study was conducted. The effect of 5 mg once daily and 15 mg twice daily compared to placebo was evaluated in a total of 56 patients. Numerical positive treatment effects were seen in specific tests that measured visual learning and working memory. A change was observed in verbal learning favoring placebo. Importantly, the trial achieved a statistically significant positive treatment effect on a secondary endpoint, which was the UCSD (University of California at San Diego) Performance-based Skills Assessment (UPSA) test. The UPSA scale assesses the functional capacity of skills for daily living and has been recognized by drug regulators as an appropriate co-primary endpoint in patients suffering from schizophrenia-related cognitive impairment.

Given the expression of ADNP in blood cells, F. J. Quintana et al. *Ann N Y Acad Sci* 1070, 500-506 (2006); R. Zamostiano et al. *J Biol Chem* 276, 708-714 (2001); M. Bassan et al. *J Neurochem* 72, 1283-1293 (1999); M. Braitch et al. *Neuroimmunomodulation* 17, 120-125 (2009), the involvement of ADNP and ADNP2 is survival, M. Kushnir et al. *J Neurochem* 105, 537-545 (2008), our results showing that NAP can serve as a replacement to ADNP imbalance, S. Y. Chen et al. *Dev Neurosci* 27, 13-19 (2005); M. Pascual and C. Guerri. *J Neurochem* 103, 557-568 (2007); I. Vulih-Shultzman et al. *J Pharmacol Exp Ther* 323, 438-449 (2007), it is claimed that ADNP/ADNP2 ratios in blood samples and CSF samples will allow us to advance toward preventative and personalized medicine with ADNP replacement therapy (NAP-davunetide) or other neuroprotective compounds and provide tools for better assessments of clinical trial results. A sensitive assay will also allow increasing the responder rates and will provide for preventative treatment.

Materials and Methods

Lymphocytes

Human lymphocytes were isolated from 10 ml of venous blood using the Ficoll Paque method (E. de Rock and N. Taylor, *J Immunol Methods.* 1977; 17(3-4):373-4; I. McCauley and P. E. Hartmann, *J Immunol Methods.* 1982; 50(1): 33-8.).

RNA Extraction

Total RNA from controls (n=13) and schizophrenia (n=13) patients was purified from blood specimens (lymphocytes) using Trizol reagent (Sigma) with further purification of the RNA phase by the RNeasy Kit (Qiagen, Valencia, Calif.). The purity and concentration of the RNA were determined spectrophotometrically according to the absorbance at 260 nm and at 280 nm (GeneQuant II, Pharmacia Biotech, Piscataway, N.J.). RNA integrity was further determined by electrophoresis on 1% agarose gel and staining with ethidium bromide. The quantity of RNA was determined by measuring OD260 with a NanoDrop spectrophotometer (NanoDrop Technologies, Wilmington, Del.).

Reverse Transcription and Quantitative Real Time PCR

Samples with same amount of total RNA were used to synthesize single-strand cDNA using SuperScript III RNase H Reverse Transcriptase (Invitrogen, Carlsbad, Calif.) and a random hexamers adaptor primer according to the manufacturer's instructions. Primer pairs (Table 1) were designed using the primer 3 web interface (website: frodo.wi.mit.edu/primer3/) and synthesized by Sigma-Genosys (The Woodlands, DQ. Real Time PCR was performed using the FAST SYBR® Green PCR Master Mix and StepOnePlus™ Real-Time PCR System Sequence Detection System instrument and software (Applied Biosystems, Foster City; CA) using the default thermocycler program for all genes: Real-time PCR reactions were carried out in a total volume of 10 µl in a 96-well plate (Applied Biosystems) containing 5 µl of X2 FAST SYBR® Green PCR Master Mix and 300 nM of each sense and antisense primers. Data was analyzed using the Data Assist™ v2.0 Software (Applied Biosystems, Foster City, Calif.). The comparative Ct method was used for quantification of transcripts, compares the Ct value of target gene to a house-keeping gene in a single sample. The results displayed as $2^{\wedge}-\Delta CT$-changes $\Delta CT$ values to linear values.

Results and Discussions

Increased Level of ADNP1 and ADNP2 Transcript in Schizophrenic Patients

Figure 5:
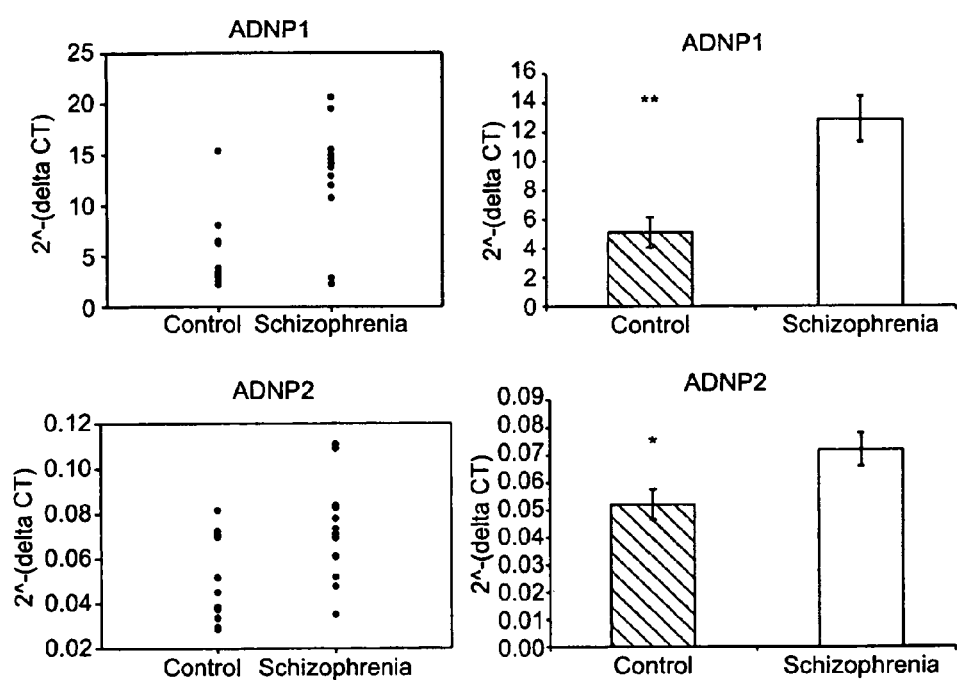
FIG. 5: ADNP (termed ADNP1) and ADNP2 levels in schizophrenia patients: comparison with age-matched normal population. Left panel, scatter plot; right panel, bar graph.

Comparisons of ADNP transcript level (termed ADNP1 in FIG. 5) showed a significant increase in the blood of the schizophrenia subjects. Thus, The ADNP1 $2^{\wedge}$-(delta CT) average value was significantly increased in the schizophrenia patients (P-value=0.0002). This increase was quite evenly distributed between the subjects (left panel). A similar increase, albeit slightly lower was observed with ANDP2 in the lymphocytes of the schizophrenia samples. Thus, the ADNP2 $2^{\wedge}$-(delta CT) average value was significantly increased in the schizophrenia patients (P-value=0.018).

Figure 6:
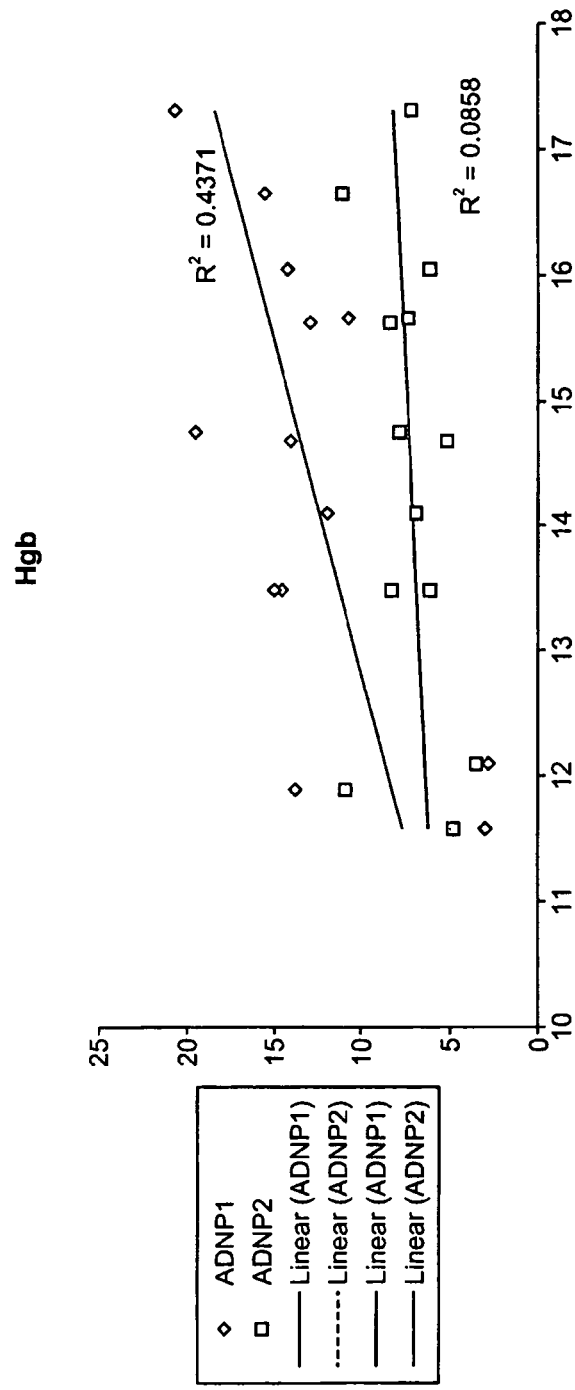
FIG. 6: Results were plotted against the levels of hemoglobin showing a higher correlation for ADNP than for ADNP2, suggesting a potential cross regulation (the results for ADNP2 are multiplied by 100 to fit on the same graph).

There also seems to be a correlation between the ADNP or ADNP2 expression level and the hemoglobin level, indicating a possible cross regulation. A higher correlation is observed for ADNP (ADNP1) than for ADNP2. See FIG. 6.

Example 3

Tauopathy and Alzheimer's Disease (AD)

1. Does ADNP Expression Change as a Consequence of AD Progression and can ADNP Level in Peripheral Blood Cells Serve as a Diagnostic Marker for AD in Patients?

In the AD PS1×APP transgenic mouse model [PS1 (M146L)×APP(751SL)], ADNP mRNA expression in 6-month-old transgenic hippocampus was higher than in wild-type (WT) mice. A similar extent of hippocampal ADNP expression was observed in 18-month-old WT and PS1×APP mice, in contrast to the differential expression level at 6 months. Thus, hippocampal ADNP expression is changing related to AD pathology, serving as a potential compensatory mechanism and a marker for disease progression (R. Femandez-Montesinos et al. *J Mol Neurosci* 2010; 41:114-20.

In a mouse model of human tauopathy (P301L), termed rTg4510, M. Ramsden et al., *J Neurosci* 25, 10637-10647 (2005), levels of several soluble phosphorylated tau species were highest at 1 month relative to later time points, this material was cleared by 3 months, while heat shock protein expression increased with normal aging, this process was accelerated in rTg4510 mice. Moreover, endogenous mouse tau turnover was slowed in response to human tau overexpression, and this endogenous tau adopted disease-related properties (C. Dickey et al. *Am J Pathol* 174, 228-238 (2009)). The onset of memory deficit was first observed at 2.5 months and was significant at 4 months. Mature neurofibrillary tangles, detected by Bielschowsky silver stain, appeared at 4 months and significant neuronal loss was estimated by stereology at 5.5 months (M. Ramsden et al. *J Neurosci* 25, 10637-10647 (2005)). To correlate between the pathology in this tauopathy model with ADNP expression, we performed comparative protein analysis by western blots. Our results (FIG. 3) show an increase in ADNP immunoreactivity (A. Pinhasov et al. *Brain Res Dev Brain Res* 144, 83-90 (2003)) in the nuclear fraction (prepared as in S. Goldberg et al. *J Neurochem* 111, 72-79 (2009)) obtained from 3-month-old mice (cerebral cortex tissue) compared to WT mice.

In contrast, at 5.5 months there were similar amounts of ADNP (with an apparent increase in the control mice and an apparent decrease in the transgenic mice compared to 3-month-old mice and the decrease continued at 9 month of age (FIG. 3A). These results place ADNP as a surrogate diagnostic tool for AD progression while corroborating the need for ADNP-like replacement therapy.

The ADNP derived neuroprotective peptide, NAP that has shown ADNP replacement properties (M. Pascual and C. Guerri. *J Neurochem* 103, 557-568 (2007; I. Vulih-Shultzman et al. *J Pharmacol Exp Ther* 323, 438-449 (2007)) is currently under clinical development (generic name, davunetide) by Allon Therapeutic Inc. showing cognitive protection in patients suffering from amnestic mild cognitive impairment (prodromal AD patients) (I. Gozes et al. *Curr Alzheimer Res* 6, 455-460 (2009)) and improving daily activities and visual memory in schizophrenic patients (D. C. Javitt *Schizophrenia Research* 2010; 117, 118-9). The ADNP gene is localized to human chromosome 20q13.13-13.2 (R. Zamostiano et al. *J Biol Chem* 276, 708-714 (2001)) a region that was associated with cognitive function (W. Borozdin et al. *Hum Mutat* 28, 830 (2007); I. Vulih-Shultzman et al. *J Pharmacol Exp Ther* 323, 438-449 (2007)). The ADNP homologue, ADNP2 (R. Zamostiano et al. *J Biol Chem* 276, 708-714 (2001)) that is required for cell viability (M. Kushnir et al. *J Neurochem* 105, 537-545 (2008)), but does not contain the NAP motif (R. Zamostiano et al. *J Biol Chem* 276, 708-714 (2001)) is assigned to chromosome 18q23 (M. Kushnir et al. *J Neurochem* 105, 537-545 (2008)), a region associated with psychiatric disorders (C. Van Broeckhoven and G. Verheyen. *Am J Med Genet.* 88, 263-270 (1999)). We recently discovered a high level of correlation between ADNP and ADNP2 expression in the differentiating neuro-glial mouse cell model—P19, the original source of ADNP (r=0.98, p=001), M. Bassan et al. *J Neurochem* 72, 1283-1293 (1999), (Dresner and Gozes, *Eur Neuropsychopharmacol* 2010 Jul. 1). Importantly, our quantitative real time polymerase chain reaction (qPCR) (S. Mandel et al. *J Mol Neurosci* 35, 127-141 (2008)) results showed that in the normal population aged 46.6±15.4 years (Mean±S.D.), hippocampal ADNP to ADNP2 transcript correlation was maintained r=0.931 (p<0.001, n=14). In contrast, in the hippocampus of schizophrenia patients, this correlation was dramatically decreased to r=0.637 (p=0.014, n=14) and the decrease was significantly associated with disease duration with ~2-fold increase in the relative ADNP2 expression. In the frontal cortex of the same schizophrenia patients there was a much higher correlation between ADNP and ADNP2 (r=0.854, p<0.001, n=12) than in the hippocampus, a phenomenon which may reflect difference in ADNP and ADNP2 equilibrium between different brain regions. Thus, an imbalance in ADNP/ADNP2 expression may impact disease progression in schizophrenia (Dresner and Gozes, supra). An association between AD and schizophrenia is that both diseases exhibit cognitive deficits, both show synaptic dysfunctions and microtubule dysfunction (A. Andrieux et al. *Genes Dev* 16, 2350-2364 (2002); M. Niethammer et al. *Neuron* 28, 697-711 (2000)), prolonged antipsychotic drug treatment causes tauopathy (C. X. Gong et al. *Brain Res* 741, 95-102 (1996)), and both diseases are associated with deregulation of the epigenome (P. Narayan and M. Dragunow. *Br J Pharmacol* (2009)). The relative expression of ADNP/ADNP2 in AD and PSP brain, CSF and blood samples in association with disease progression will lead toward better prediction of the outcome of NAP (davunetide) disease modification, an example of biomarkers addressing preventative personalized treatment.

Our studies will encompass three different clinical sources for ADNP: A] Post mortem AD brains and relevant age and gender-matched controls: brain areas will include (in a separate form): hippocampus, cortex, cerebellum, and will be used for mRNA and protein extraction (10 samples per each brain area), evaluating mild, moderate and severe disease states. RNA analysis by northern blot hybridization (R. Zamostiano et al. *J Biol Chem* 276, 708-714 (2001)) as well as qPCR using the appropriate primers (R. Zamostiano et al. *J Biol Chem* 276, 708-714 (2001)) will identify potential changes in the disease mRNA preparation that is different from control samples. In this respect, ADNP undergoes alternative splicing of an untranslated second exon (R. Zamostiano et al. *J Biol Chem* 276, 708-714 (2001)) and it is of interest to evaluate the potential association of this on disease onset and progression. Additional studies will use immunohistochemistry to precisely identify cells producing ADNP coupled to cellular distribution (nuclear and cytoplasmic/neurites (S. Mandel et al. *J Mol Neurosci* 35, 127-141 (2008)). Brains will be obtained from the John Hopkins University Brain Bank (we have collaborations with Professors. Yasuji Matsuoka and Paul Aisen (Director ADCS, UCSD, USA)(Y. Matsuoka et al. *J Mol Neurosci* 31, 165-170 (2007); Y. Matsuoka et al. *J Pharmacol Exp Ther* 325, 146-153 (2008)), Adam Boxer and Bruce Miller (PI on Allon's clinical trials in frontotemporal dementia, and Clinical Director, Memory and Aging Center (MAC) at UCSF, USA, respectively) and Judith Aharon-Peretz (Head of the "Cognitive Neurology Unit". Rambam-Health Care Campus, Haifa, Israel). B] Peripheral blood mononuclear cells (PBMCs) following published protocols. As indicated above, ADNP is expressed in PBMCs. Here, PBMCs will be isolated from healthy volunteers and patients with AD (age- and gender matched) by gradient centrifugation with Histopaque 1077 (Sigma Aldrich, Dorset, UK). $10^6$ cells will be surface-stained with 5 µl antiCD4 (ECD, T-helper cells), 5 µl CD25 (PC5, regulatory T cells), 3 µl CD3 (PC7, T helper (Th) and T cytotoxic (Tc) lymphocytes), 5 µl CD19 (PE; B cells—all from Beckman Coulter, Fullerton, Calif., USA). Natural killer cells will be identified by (CD3−CD56+) and the monocyte-macrophage lineage by (CD14). PBMCs will be kept dark on ice for 30 min. Cells will be incubated in 500 µl of 2% formaldehyde at room temperature for a further 5 min. Cells will be washed in 1 ml PBA (phosphate-buffered saline, 0.5% bovine serum, 1% sodium azide) and resuspended in 1 ml saponin buffer (PBA, 0.1% Saponin) for permeabilization. Cells will be washed twice in saponin buffer containing 10% FCS. Cells will be then stained with 1 µg (5 µl) of the primary ADNP antibody (Abcam, Cambridge, Mass., USA), incubated for 30 min, and washed in saponin buffer. Cells will be then incubated with 5 µl of the secondary antibody conjugated to FITC (Abcam), washed with saponin buffer, and fixed with 0.5% formaldehyde. Published blocking experiments showed that incubation of the anti-ADNP (NAP) antibody with excess NAP peptide consistently reduced fluorescence staining by >80% (M. Braitch et al. *Neuroimmunomodulation* 17, 120-125 (2009)). The various cell types will be separated by flow cytometry (M. Braitch et al. *Neuroimmunomodulation* 17, 120-125 (2009)). For RNA preparation, peripheral blood will be obtained as above. Blood samples will be incubated at room temperature for 3 h in Paxgene blood RNA tubes (PreAnalytix, UK) before processing for total RNA extraction (M. Braitch et al. *Neuroimmunomodulation* 17, 120-125 (2009)) following the manufacturer's instructions (www.EpiBio.com). Extracted RNA from each sample will be quantified (40-175 ng/µl) and quality evaluated using a spectrophotometer (ND-1000 v3.3.0; Nanodrop, Wilmington, Del., USA). RNA will be converted to cDNA and ADNP mRNA content will be measured as we published before by qPCR (S. Mandel et al. *Dev Biol* 303, 814-824 (2007; S. Mandel and I. Gozes. *J Biol Chem* 282, 34448-34456 (2007; S.

Mandel et al. *J Mol Neurosci* 35, 127-141 (2008)). Our original studies suggest ADNP synthesis in macrophages (F. J. Quintana et al. *Ann N Y Acad Sci* 1070, 500-506 (2006)) and macrophages, if mimicking the brain situation, can be used as relevant surrogate markers. To assess ADNP expression in macrophages obtained from AD patients and age-matched controls (through isolation of PBMCs by density gradient centrifugation using Ficoll methods, and deriving macrophages during cell culture (J. T. Deichen et al., *Eur J Nucl Med Mol Imaging* 30, 267-273 (2003)) and (E. de Rock and N. Taylor, *J Immunol Methods.* 1977; 17(3-4):373-4; I. McCauley and P. E. Hartmann, *J Immunol Methods.* 1982; 50(1):33-8—as above), we shall use western analyses as well as RNA quantitation as above (S. Mandel and I. Gozes. *J Biol Chem* 282, 34448-34456 (2007)). ADNP2 will be assessed side by side with ADNP to evaluate potential deviations from the control correlation. C] CSF and plasma samples will be tested for ADNP-like immunoreactivity, by western blot and enzyme-linked immunoadsorbant assay (ELISA). The ELISA protocol will be implemented as per our previous studies (I. Gozes et al. *Brain Res Dev Brain Res* 99, 167-175 (1997)) using sandwich ELISA with rabbit antibodies and mouse antibodies against ADNP that are prepared in our laboratory (R. Zamostiano et al. *J Biol Chem* 276, 708-714 (2001)) and are also commercially available (S. Mandel et al. *J Mol Neurosci* 35, 127-141 (2008)).

A major question to address here is: are ADNP and ADNP2 transcripts differentially expressed in cells that are derived from AD samples (localization and post-translational modifications)? Post-translational modification that will be assessed include phosphorylation (with pan antibodies against phosphate sites), glycosylation and polyADP ribosylation (S. Goldberg et al. *J Neurochem* 111, 72-79 (2009; L. Visochek et al. *J Neurosci* 25, 7420-7428 (2005)). We have shown before that polyADP ribosylation is associated with chromatin remodeling important for learning and memory and changes found in ADNP expression may underlie in part the dementia outcome of the disease. Further questions to be addressed: Will ADNP expression constitute a diagnostic marker of disease progression in the human situation? D] Our studies will further test the potential effect of NAP (davunetide) on ADNP and ADNP2 expression in human PBMCs. For studies of the effect of NAP on lymphocyte ADNP expression, $10^6$ PBMCs will be stimulated in vitro with 1 μg/ml anti-CD3 and anti-CD28 (Ab Beckman Coulter, Roissy, France), mimicking T-cell activation or 20 ng/ml phorbol ester, phorbol 12,13-dibutyrate (PDB) and the calcium ionophore, ionomycin (5 μg, Sigma Aldrich) also mimicking T-cell activation with or without increasing concentrations of NAP (0, 0.25, 0.5 and 1 μg/ml); 10 μg/ml of brefeldin will be added 8 h prior to intracellular staining with anti-ADNP, or prior to mRNA extraction. Cells will be incubated for 18 h at 37° C., 5% $CO_2$. Intracellular staining for ADNP-conjugated to FITC (5 μl) and surface staining with anti-CD69 will determine T cell activation. Cells will be centrifuged and fixed with 0.5% formaldehyde. Data acquisition will be performed on a Beckman Coulter flow cytometer and analyzed by using the WinMDI software. RNA expression studies will be performed as before, also on quiescent cells (S. Mandel et al. *Dev Biol* 303, 814-824 (2007); S. Mandel and I. Gozes. *J Biol Chem* 282, 34448-34456 (2007); S. Mandel et al. *J Mol Neurosci* 35, 127-141 (2008)).

Figure 4A:
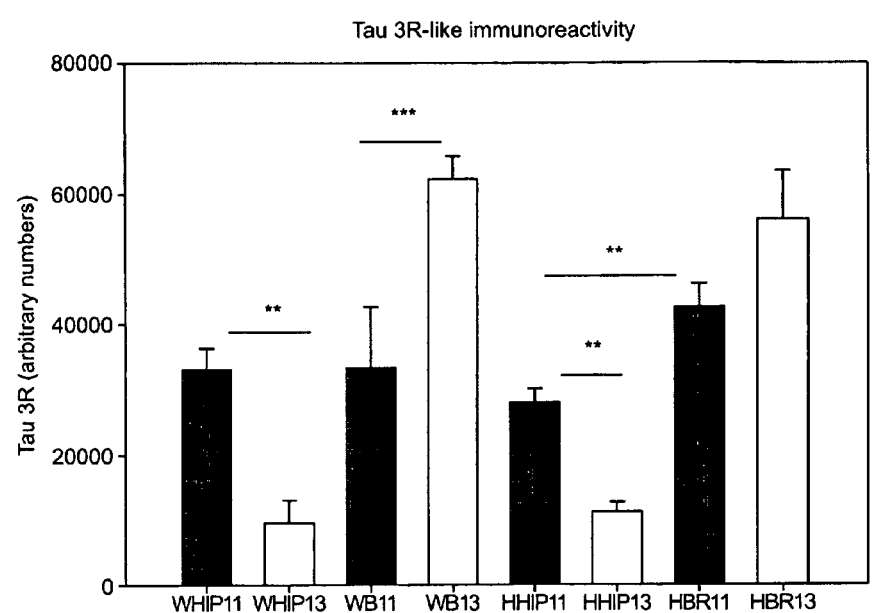
FIG. 4: A. Differential regulation of tau 3R expression in ADNP-deficient mice in comparison to control ADNP intact mice. Experiments were conducted using semi-quantitative western blot analyses. Both ADNP+/+ (W) and ADNP+/− mice (H) expressed significantly higher amounts of tau 3R at 11 months (WHIP11 or HHIP11) compared to 13 months (WHIP13 or HHIP13) in their hippocampus (HIP). In contrast, in the rest of the brain (excluding hippocampus, cerebellum and cerebral cortex) the 13-month-old ADNP+/+ mice (WB13) expressed increased levels of tau 3R compared to 11-month-old mice (WB11). In addition, the rest of the brain of 11-month-old ADNP+/− mice (HBR11) expressed higher amounts of tau 3R compare to hippocampus at the same age (HHIP11) and similar results were obtained for 13 months in both the ADNP+/+ and the ADNP+/− mice (p<0.01; *p<0.001). B. Comparison between the expression of tau 3 repeat and tau 4 repeat at the level of the proteins shows deregulation in ADNP+/− mice. C. Significant changes in the relative tau3R/4R mRNA levels as a consequence of ADNP-deficiency (P<0.03).

2. Do Changes in ADNP Expression Result in Differential Tau Processing (3R vs. 4R):

We have developed a model of deficient ADNP expression, the ADNP+/− mouse (I. Vulih-Shultzman et al. *J Pharmacol Exp Ther* 323, 438-449 (2007)). In this model, we have observed increased tau hyperphosphorylation coupled to tangle-like structure formation and neuronal cell death. Tau pathology has been associated with deregulation of alternative splicing and in AD and other taupathies (C. Dickey et al. *Am J Pathol* 174, 228-238 (2009)) and the question is whether changes in ADNP expression are associated with changes in tau splicing patterns. Tau expression in ADNP+/− mice and in AD samples will be analyzed by western analysis (Y. Matsuoka et al. *J Mol Neurosci* 31, 165-170 (2007); Y. Matsuoka et al. *J Pharmacol Exp Ther* 325, 146-153 (2008)) using tau-repeat specific antibodies (mouse monoclonal antibody tau5, MBL International Corporation, Woburn, Mass., USA; mouse monoclonal anti tau RD4 (4-repeat isoform) and mouse monoclonal anti tau RD3 (3-repeat isoform, Millipore Corporation, Billerica, Mass., USA). Results will be verified by RT-PCR analysis using specific tau RNA probes. If a change will be observed, the possible ameliorative effect of NAP will be studied as well, questioning whether NAP treatment changes the patterns of expression of tau. A preliminary study was performed on ADNP+/+ mice and ADNP+/− (I. Vulih-Shultzman et al. *J Pharmacol Exp Ther* 323, 438-449 (2007)). The study aimed to check the potential effect of reduced ADNP on the expression of tau 3R in mice at 11 and 13 months (4 mouse groups, n=3-4 mice per group). Brain regions used included the hippocampus and other brain areas excluding the cerebral cortex, hippocampus and cerebellum. Heat stable proteins including soluble tau were prepared as before (Y. Matsuoka et al. *J Pharmacol Exp Ther* 325, 146-153 (2008); N. Shiryaev et al. *Neurobiol Dis* 34, 381-388 (2009)) and analyzed for tau 3R content with specific antibodies (above). FIG. 4A shows preliminary results suggesting differential expression of tau.

Figure 4B:
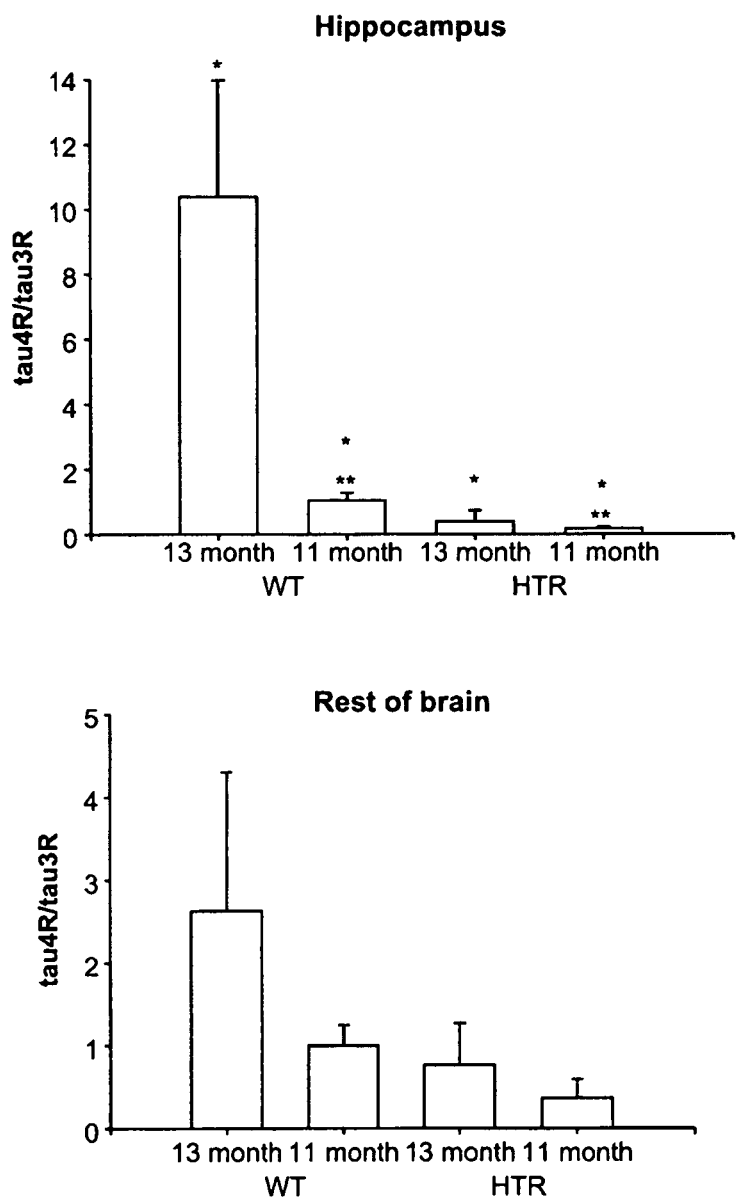

Comparison between the expression of tau 3 repeat and tau 4 repeat at the level of the proteins shows deregulation in ADNP+/− mice as depicted in FIG. 4B. Tau 4 repeat was identified by specific antibodies, as indicated: mouse monoclonal anti tau RD4 (4-repeat isoform) and mouse monoclonal anti tau RD3 (3-repeat isoform, Millipore Corporation, Billerica, Mass.).

In the hippocampus there is a significant increase in tau 4R/3R ration as a consequence of ADNP deficiency, at both ages tested, P<0.05, this increases with aging in both control mice as well as in the ADNP+/− mice, P<0.02. These results indicate a tight correlation between ADNP expression and tau splicing in the hippocampus. Tau splicing is tightly associated with tauopathies and cognitive status (see, e.g., Gozes I. *Curr Alzheimer Res.* 2010 Aug. 2. [Epub ahead of print]; Shiryaev N. et al., *J Neurosci Res.* 2010 September; 88(12):2727-35).

Figure 4C:
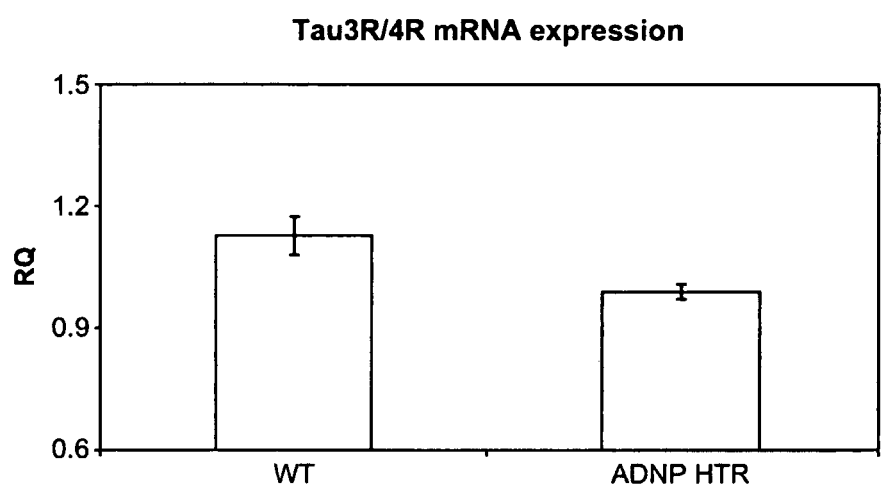

These results were corroborated at the RNA level and were apparent already at 9 months of age (quantitative real time PCR was performed as above with mouse-specific primers. Using the ADNP-deficient model described by Vulih et al., (I. Vulih-Shultzman et al., *J Pharmacol Exp Ther* 323, 438-449 (2007)) as seen in FIG. 4—lower panel in this application, significant changes in the relative tua3R/4R mRNA levels as a consequence of ADNP-deficiency (P<0.03) were found.

3. Is there a Specific ADNP Haplotype Associated with Tauopathy-Chromosome Sequencing in AD:

We have originally identified the sequence of the human ADNP gene as shown in Table I in a 2001 publication (R. Zamostiano et al. *J Biol Chem* 276, 708-714 (2001)). The human ADNP gene contains 5 exons. The estimated gene size is 40,647 base pairs. A CpG island that stretches over 1135 bases as predicted by GRAIL was observed around exon 1 (69% GC). As particularly CG-rich dinucleotides have been previously associated with promoter regions, we tested this sequence using promoter prediction programs TSSW and TSSG. Results gave low scoring promoter [TSSW at base 106 with LDF 5.69 (LDF 5 statistical promoter score. 4.00 indicates a potential promoter); TSSG gave no promoter]. Alternative splicing of the second exon has been observed in expressed sequence tags (AI827420 and AW007743). Only the three 3'-exons are protein-coding. Table II in the same manuscript, R. Zamostiano et al. *J Biol Chem* 276, 708-714 (2001), identifies several polymorphic sites on the ADNP gene and it is our intention now to decipher weather these (or more) could be associated with AD predisposition. As indicated above, we mapped the ADNP gene locus to chromosome 20q13.13-13.2 (R. Zamostiano et al. *J Biol Chem* 276, 708-714 (2001)) that is flanked by diabetes type II-linked genes (T. Klupa et al. *Diabetes* 49, 2212-2216 (2000)). The ADNP gene is separated upstream by 3438 base pairs from DPMI (dolichyl-phosphate mannosyltransferase polypeptide 1 catalytic subunit, D20S196; website: ncbi.nlm.nih.gov/genome/sts/sts.cgi?uid_57739) that has been linked to diabetes type II (p<0.00010). We now plan complete sequence analysis of the ADNP gene region and flanking regions in the samples analyzed above for RNA/protein expression to obtain a complete picture of ADNP gene variability and association with AD, similar studies will be carried out for ADNP2. We shall use the Tel Aviv University deep sequencers based on the Illumina (Solexa) Genome Analyzer IIx sequencing machine.

4. Are there Specific Regulatory Molecules Associated with ADNP Expression and AD?

Parallel RNA samples obtained for ADNP and tau analysis will be analyzed for microRNA expression (N. Shomron. *Eur J Cancer* 45 Suppl 1, 388-390 (2009)) and will be classified using bioinformatics tools (S. Artzi et al. *BMC Bioinformatics* 9,39 (2008)).

All patents, patent applications, and other publications, including GenBank Accession Numbers, cited in this application are incorporated by reference in the entirety for all purposes.

---

What is claimed is:

1. A method for assessing ADNP expression in a biological sample taken from a subject, comprising the steps of:
   (1) performing an assay to determine ADNP1 mRNA level in the sample;
   (2) performing an assay to determine ADNP2 mRNA level in the sample; and
   (3) calculating the ratio of the ADNP1 mRNA level obtained in step (1) to the ADNP2 mRNA level obtained in step (2), wherein each of steps (1) and (2) comprises performing a reverse transcriptase polymerase reaction (RT-PCR), and wherein the primer set of SEQ ID NO: 1 and SEQ ID NO: 2 is used in step (1).

2. The method of claim 1, wherein the sample is a brain sample, a blood sample, or a cerebrospinal fluid (CSF) sample.

3. The method of claim 2, wherein the brain sample is taken from the hippocampus of the patient.

4. The method of claim 2, wherein the brain sample is taken from the frontal cortex of the patient.

5. The method of claim 2, wherein the blood sample is a whole blood, plasma, or serum sample.

6. The method of claim 1, wherein the PCR in steps (1) and (2) is a quantitative real time PCR.

7. The method of claim 6, wherein SYBER GREEN is used in the quantitative real time PCR.

8. The method of claim 1, further comprising repeating steps (1) through (3) at later time with a second biological sample, the second biological sample being the same type of sample as the first biological sample and taken from the same subject.

9. The method of claim 1, wherein the subject is an individual whose state of neurodegeneration or a metal disorder is being assessed.

10. A method for assessing ADNP expression in a biological sample taken from a subject, comprising the steps of:
    (1) performing an RT-PCR to determine ADNP1 mRNA level in the sample, wherein a primer of SEQ ID NO:1 or SEQ ID NO:2 is used in the PCR;
    (2) performing an RT-PCR to determine ADNP2 mRNA level in the sample; and
    (3) calculating the ratio of the ADNP1 mRNA level obtained in step (1) to the ADNP2 mRNA level obtained in step (2).

11. The method of claim 10, wherein the sample is a brain sample, a blood sample, or a cerebrospinal fluid (CSF) sample.

12. The method of claim 11, wherein the brain sample is taken from the hippocampus of the patient.

13. The method of claim 11, wherein the brain sample is taken from the frontal cortex of the patient.

14. The method of claim 11, wherein the blood sample is a whole blood, plasma, or serum sample.

15. The method of claim 10, wherein the PCR in steps (1) and (2) is a quantitative real time PCR.

16. The method of claim 15, wherein SYBER GREEN is used in the quantitative real time PCR.

17. The method of claim 10, further comprising repeating steps (1) through (3) at later time with a second biological sample, the second biological sample being the same type of sample as the first biological sample and taken from the same subject.

18. The method of claim 10, wherein the subject is an individual whose state of neurodegeneration or a metal disorder is being assessed.

* * * * *

SEQUENCE LISTING

<160> NUMBER OF SEQ ID NOS: 17

<210> SEQ ID NO 1
<211> LENGTH: 23
<212> TYPE: DNA
<213> ORGANISM: Artificial Sequence
<220> FEATURE:
<223> OTHER INFORMATION: synthetic primer for human activity-dependent
      neuroprotective protein (ADNP), transcript variant
      1, activity-dependent neuroprotector homeobox,
      ADNP homeobox 1, ADNP1

<400> SEQUENCE: 1
acttacgaaa aaccaggact atc                                           23

<210> SEQ ID NO 2
<211> LENGTH: 17
<212> TYPE: DNA
<213> ORGANISM: Artificial Sequence
<220> FEATURE:
<223> OTHER INFORMATION: synthetic primer for human activity-dependent
      neuroprotective protein (ADNP), transcript variant
      1, activity-dependent neuroprotector homeobox,
      ADNP homeobox 1, ADNP1

<400> SEQUENCE: 2
gacattgcgg aaatgac                                                  17

<210> SEQ ID NO 3
<211> LENGTH: 25
<212> TYPE: DNA
<213> ORGANISM: Artificial Sequence
<220> FEATURE:
<223> OTHER INFORMATION: synthetic primer for human  ADNP2, ADNP
      homeobox 2, zinc finger protein 508 (ZNF508)

<400> SEQUENCE: 3
gaaagaaagt gagatatcga acaaa                                         25

<210> SEQ ID NO 4
<211> LENGTH: 21
<212> TYPE: DNA
<213> ORGANISM: Artificial Sequence
<220> FEATURE:
<223> OTHER INFORMATION: synthetic primer for human  ADNP2, ADNP homeobox 2, zinc finger protein 508 (ZNF508)

<400> SEQUENCE: 4
tggtcaattt catcttcatg g                                          21

<210> SEQ ID NO 5
<211> LENGTH: 21
<212> TYPE: DNA
<213> ORGANISM: Artificial Sequence
<220> FEATURE:
<223> OTHER INFORMATION: synthetic primer for human TATA box binding
      protein (TBP), transcript variant 1, TATA box binding protein
      N-terminal domain, TATA box factor, TATA sequence-binding protein,
      transcription initiation factor TFIID TBP subunit (TFIID), GTF2D,
      HDL4, SCA17

<400> SEQUENCE: 5
ggagccaaga gtgaagaaca g                                          21

<210> SEQ ID NO 6
<211> LENGTH: 20
<212> TYPE: DNA
<213> ORGANISM: Artificial Sequence
<220> FEATURE:
<223> OTHER INFORMATION: synthetic primer for human TATA box binding
      protein (TBP), transcript variant 1, TATA box binding protein
      N-terminal domain, TATA box factor, TATA sequence-binding protein,
      transcription initiation factor TFIID TBP subunit (TFIID), GTF2D,
      HDL4, SCA17

<400> SEQUENCE: 6
cacagctccc caccatattc                                            20

<210> SEQ ID NO 7
<211> LENGTH: 24
<212> TYPE: DNA
<213> ORGANISM: Artificial Sequence
<220> FEATURE:
<223> OTHER INFORMATION: synthetic primer for mouse tubulin beta3
      (Tubb3), tubulin beta 3 class II, betaIII-tubulin, M(beta)3

<400> SEQUENCE: 7
aactttatct ttggtcagag tggt                                       24

<210> SEQ ID NO 8
<211> LENGTH: 20
<212> TYPE: DNA
<213> ORGANISM: Artificial Sequence
<220> FEATURE:
<223> OTHER INFORMATION: synthetic primer for mouse tubulin beta3
      (Tubb3), tubulin beta 3 class II, betaIII-tubulin, M(beta)3

<400> SEQUENCE: 8
tgcaggcagt cacaattctc                                            20

<210> SEQ ID NO 9
<211> LENGTH: 19
<212> TYPE: DNA
<213> ORGANISM: Artificial Sequence
<220> FEATURE:
<223> OTHER INFORMATION: synthetic primer for mouse glial fibrillary
      acidic protein (GFAP), transcript variant 1, intermediate
      filament protein, AI836096

<400> SEQUENCE: 9
gaaaaccgca tcaccattc                                             19

```
<210> SEQ ID NO 10
<211> LENGTH: 20
<212> TYPE: DNA
<213> ORGANISM: Artificial Sequence
<220> FEATURE:
<223> OTHER INFORMATION: synthetic primer for mouse glial fibrillary
      acidic protein (GFAP), transcript variant 1, intermediate
      filament protein, AI836096

<400> SEQUENCE: 10
ccttctgaca cggatttggt                                              20

<210> SEQ ID NO 11
<211> LENGTH: 21
<212> TYPE: DNA
<213> ORGANISM: Artificial Sequence
<220> FEATURE:
<223> OTHER INFORMATION: synthetic primer for mouse activity-dependent
      neuroprotective protein (ADNP), activity-dependent
      neuroprotector homeobox, AA589558, mKIAA0784

<400> SEQUENCE: 11
acgaaaaatc aggactatcg g                                            21

<210> SEQ ID NO 12
<211> LENGTH: 21
<212> TYPE: DNA
<213> ORGANISM: Artificial Sequence
<220> FEATURE:
<223> OTHER INFORMATION: synthetic primer for mouse activity-dependent
      neuroprotective protein (ADNP), activity-dependent
      neuroprotector homeobox, AA589558, mKIAA0784

<400> SEQUENCE: 12
ggacattccg gaaatgactt t                                            21

<210> SEQ ID NO 13
<211> LENGTH: 20
<212> TYPE: DNA
<213> ORGANISM: Artificial Sequence
<220> FEATURE:
<223> OTHER INFORMATION: synthetic primer for mouse ADNP homeobox 2,
      ADNP2, zinc finger protein 508 (Zfp508), mKIAA0863, BC024969

<400> SEQUENCE: 13
ggaaagaaag cgagataccg                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic primer for mouse ADNP homeobox 2,
      ADNP2, zinc finger protein 508 (Zfp508), mKIAA0863, BC024969

<400> SEQUENCE: 14
tcctggtcag cctcatcttc                                              20

<210> SEQ ID NO 15
<211> LENGTH: 22
<212> TYPE: DNA
<213> ORGANISM: Artificial Sequence
<220> FEATURE:
<223> OTHER INFORMATION: synthetic primer for mouse hypoxanthine-guanine
      phosphoribosyl transferase 1 (HPRT1, HPRT B,
      HPGRT, HGPRTase), C81579

<400> SEQUENCE: 15
```

-continued

```
ggatttgaat cacgtttgtg tc                                              22

<210> SEQ ID NO 16
<211> LENGTH: 21
<212> TYPE: DNA
<213> ORGANISM: Artificial Sequence
<220> FEATURE:
<223> OTHER INFORMATION: synthetic primer for mouse hypoxanthine-guanine
      phosphoribosyl transferase 1 (HPRT1, HPRT B,
      HPGRT, HGPRTase), C81579

<400> SEQUENCE: 16
caggactcct cgtatttgca g                                               21

<210> SEQ ID NO 17
<211> LENGTH: 8
<212> TYPE: PRT
<213> ORGANISM: Artificial Sequence
<220> FEATURE:
<223> OTHER INFORMATION: synthetic human activity-dependent
      neuroprotective protein (ADNP) 8-amino acid peptide fragment, NAP
      motif neuroprotectant and neurotrophic factor

<400> SEQUENCE: 17

Asn Ala Pro Val Ser Ile Pro Gln
1               5
```